United States Patent
Soerensen et al.

(10) Patent No.: US 9,232,812 B2
(45) Date of Patent: *Jan. 12, 2016

(54) APPARATUS AND METHOD FOR HYDROLYSIS OF A PROTEIN CONTAINING RAW MATERIAL AND APPLICATION OF THE RESULTING HYDROLYSIS PRODUCTS

(75) Inventors: Stig Soerensen, Kgs. Lyngby (DK); Kjartan Sandnes, Bones (NO); Harald Hagen, Storebo (NO); Karstein Pedersen, Storebo (NO)

(73) Assignee: MARINE BIOPRODUCTS A.S., Storebo (NO)

( * ) Notice: Subject to any disclaimer, the term of this patent is extended or adjusted under 35 U.S.C. 154(b) by 619 days.

This patent is subject to a terminal disclaimer.

(21) Appl. No.: 12/909,587

(22) Filed: Oct. 21, 2010

(65) Prior Publication Data

US 2011/0033889 A1 Feb. 10, 2011

Related U.S. Application Data

(62) Division of application No. 10/725,039, filed on Dec. 2, 2003, now Pat. No. 8,173,014.

(30) Foreign Application Priority Data

Dec. 2, 2002 (DK) .............................. 2002 01859

(51) Int. Cl.
| C12P 21/06 | (2006.01) |
| A23J 1/10 | (2006.01) |
| A23J 1/00 | (2006.01) |
| A23J 1/04 | (2006.01) |
| A23J 3/34 | (2006.01) |

(52) U.S. Cl.
CPC .. *A23J 1/10* (2013.01); *A23J 1/002* (2013.01); *A23J 1/04* (2013.01); *A23J 3/341* (2013.01); *A23J 3/346* (2013.01); *Y10T 137/8622* (2015.04)

(58) Field of Classification Search
None
See application file for complete search history.

(56) References Cited

U.S. PATENT DOCUMENTS

| 2,595,180 A | 4/1952 | Vincent |
| 2,614,110 A | 10/1952 | Davis |
| 2,806,790 A | 9/1957 | Bedford |
| 2,832,684 A | 4/1958 | Simes |
| 2,857,278 A | 10/1958 | Milner |
| 2,934,433 A | 4/1960 | Brucklesby et al. |
| 3,041,174 A | 6/1962 | Ehlert |
| 3,096,234 A | 7/1963 | Armstrong et al. |
| 3,116,682 A | 1/1964 | Mackenzie |
| 3,170,794 A | 2/1965 | Jeffreys et al. |
| 3,245,759 A | 4/1966 | Eweson |
| 3,249,442 A | 5/1966 | Keyes et al. |
| 3,252,962 A | 5/1966 | Whaley et al. |
| 3,434,920 A | 3/1969 | Green |
| 3,497,364 A | 2/1970 | Overtou |
| 3,547,652 A | 12/1970 | Jeffreys |
| 3,561,973 A | 2/1971 | Rutman |
| 3,580,725 A | 5/1971 | Kaster |
| 3,598,606 A | 8/1971 | Spinelli et al. |
| 3,692,538 A | 9/1972 | Moss et al. |
| 3,697,285 A | 10/1972 | Faith et al. |
| 3,796,811 A | 3/1974 | Huth et al. |
| 3,798,126 A | 3/1974 | Gasser et al. |
| 3,804,964 A | 4/1974 | Hogstedt et al. |
| 3,857,966 A | 12/1974 | Feldman et al. |
| 3,861,293 A | 1/1975 | Buffa et al. |
| 3,924,005 A | 12/1975 | Bosund et al. |
| 4,036,993 A | 7/1977 | Ikeda et al. |
| 4,091,003 A | 5/1978 | Bosund et al. |
| 4,163,009 A | 7/1979 | Filstrup |
| 4,176,199 A | 11/1979 | Vollmer et al. |
| 4,212,889 A | 7/1980 | Fuentevilla |
| 4,220,723 A | 9/1980 | Eckmayer et al. |
| 4,286,884 A | 9/1981 | Retrum |
| 4,344,976 A | 8/1982 | Bladh |
| 4,389,423 A | 6/1983 | Madsen |

(Continued)

FOREIGN PATENT DOCUMENTS

| CN | 1157694 A | 8/1997 |
| DE | 25 26 879 | 12/1976 |

(Continued)

OTHER PUBLICATIONS

Parr Reactor Company © 1990-2013. 5400 Continuous Flow Tubular Reactors | Parr Instrument Company, pp. 1-4, http://www.parrinst.com/products/specialty-custom-systems/5400-continuous-flow-tubular. Printed Jan. 1, 2013.*

(Continued)

Primary Examiner — Debbie K Ware
Assistant Examiner — Kailash C Srivastava
(74) Attorney, Agent, or Firm — Zareefa B. Flener; Flener IP Law

(57) ABSTRACT

Apparatus and methods for hydrolyzing protein-containing raw material into water soluble protein and other products. The apparatuses and methods comprise an optional collection or processing stage in which protein-containing raw material, such as fish or animal carcasses from food production plants, are collected and optionally processed. The raw material is then reacted with one or more enzymes to hydrolyze the protein present, after which the one or more enzymes are inactivated and the components separated. The processes and apparatuses, which can be run as a batch processes or, advantageously as a continuous processes, can yield water soluble protein, oils, bone meal and other products that have utility as food or food additives.

36 Claims, 9 Drawing Sheets

(56) References Cited

U.S. PATENT DOCUMENTS

| | | |
|---|---|---|
| 4,405,649 A | 9/1983 | Jeffreys et al. |
| 4,427,658 A | 1/1984 | Maubois et al. |
| 4,443,540 A | 4/1984 | Chervan et al. |
| 4,452,888 A | 6/1984 | Yamazaki et al. |
| 4,473,589 A | 9/1984 | Freeman et al. |
| 4,482,574 A | 11/1984 | Lee |
| 4,820,529 A | 4/1989 | Uchida et al. |
| 4,853,231 A | 8/1989 | Osajima et al. |
| 4,861,602 A | 8/1989 | Uchida et al. |
| 4,863,746 A | 9/1989 | Uchida et al. |
| 4,961,936 A | 10/1990 | Rubin |
| 4,963,370 A | 10/1990 | Uchida et al. |
| 4,976,973 A | 12/1990 | Shirakawa et al. |
| 5,053,234 A | 10/1991 | Anderson et al. |
| 5,113,755 A | 5/1992 | Anderson et al. |
| 5,141,763 A | 8/1992 | Hansen et al. |
| 5,162,129 A | 11/1992 | Anderson et al. |
| 5,188,729 A | 2/1993 | Krofta |
| 5,356,637 A | 10/1994 | Loosen et al. |
| 5,384,149 A | 1/1995 | Lin |
| 5,532,007 A | 7/1996 | Pedersen et al. |
| 5,549,920 A | 8/1996 | Choudhury |
| 5,552,173 A | 9/1996 | Singh et al. |
| 5,618,689 A | 4/1997 | McCarthy et al. |
| 5,772,968 A | 6/1998 | Wolfe |
| 5,853,791 A | 12/1998 | Roussel |
| 5,905,033 A | 5/1999 | Morita et al. |
| 5,957,041 A | 9/1999 | Fosbøl et al. |
| 5,972,403 A | 10/1999 | Tiller |
| 6,159,515 A | 12/2000 | Schaefer et al. |
| 6,261,608 B1 | 7/2001 | Lee et al. |
| 6,288,216 B1 | 9/2001 | Hultin et al. |
| 6,537,787 B1 | 3/2003 | Breton |
| 2002/0182290 A1 | 12/2002 | Nielsen |
| 2003/0147994 A1 | 8/2003 | Saxby et al. |

FOREIGN PATENT DOCUMENTS

| | | | |
|---|---|---|---|
| DE | 25 26 879 A1 | 12/1976 | |
| DE | 2526879 * | 12/1976 | ............... C12B 1/00 |
| EP | 0 096 902 A2 | 12/1983 | |
| EP | 0 566 877 A2 | 10/1993 | |
| EP | 0 899 327 A2 | 3/1999 | |
| FR | 2 168 259 | 8/1973 | |
| FR | 2 352 498 | 12/1977 | |
| FR | 2352498 A * | 12/1977 | ............... A23J 1/04 |
| JP | 59063140 A | 4/1984 | |
| JP | 59063144 A | 4/1984 | |
| JP | 61028370 A | 2/1986 | |
| JP | 63148985 A | 6/1988 | |
| JP | 02222641 A | 9/1990 | |
| JP | 03047051 A | 2/1991 | |
| WO | WO 93/09679 | 5/1993 | |
| WO | WO 97/43910 | 11/1997 | |
| WO | WO 01/28353 A2 | 4/2001 | |
| WO | 02087354 A1 | 11/2002 | |
| WO | WO 02/087354 A1 | 11/2002 | |
| WO | WO 02/102347 A2 | 12/2002 | |

OTHER PUBLICATIONS

Kohlbach, DE-2526879A English Translation.*
Belhomme, FR 2352498A English Translation.*
Abstract, Derwent Publications Ltd., London, GB; Class D13, AN 2001-375305 XP0902278100 and CN 1 157 694 A, Haitian Nutrient Source Co. Ltd. Yuhuan Co., Aug. 27, 1997.
Hordur G. Kristinsson et al., "Fish Protein Hydrolysates: Production, Biochemical, and Functional Properties," Critical Reviews in Food Science and Nutrition, 2000, pp. 43-81, vol. 40, No. 1.
International Search Report for International Application PCT/US03/38121, filed Feb. 12, 2003. (Applicant Green Earth Industries), European Patient Office, NL-2280, HV Rijswik, May 12, 2004.
Antwoordeonclusie in conventie en akte in reconventie houdende wijzigang van eis, Sep. 12, 2007, Rechtbank, te 's-gravenhage; Rolnummer: 2006/2378 (27 pages).
Cause-list No. 2006/2378; District Court [Arrondissementsrechtbank] in The Hague Statement of defence with respect to Green Earth's additional claim of Feb. 28, 2007 also amendment of Marine Bioproducts' counterclaim, Sep. 12, 2007 (English Translation) (16 pages).
Pleitaantekeningen van mrs. F.W.J. van der Eerden, H.M.H. Speyart en E.E. de Vos, (Green Earth Industries LLC Oral Pleadings); Feb. 22, 2008; Rechtbank te '-Gravenhage; Rolnummer: 2006/2378 (32 pages).
English Translation of Green Earth Industries LLC Oral Pleadings, F.W.J. van der, Eerden, H.M.H. Speyart and E.E. de Vos.; District court of The Hague; Feb. 22, 2008 (32 pages).
Pleitnota mrs. De Groot en Herschdorfer, (Marine Bioproducts AS Oral Pleadings); Feb. 22, 2008 Rechtbank te '-Gravenhage; Rolnummer: 2006/2378 (22 pages).
English Translation of Marine Bioproducts AS / Notes of Oral Pleadings, De Groot and Herschdorfer. District Court of The Hague; Feb. 22, 2008 (25 pages).
Judge's hand Written Records of Oral Hearing (Green Earth Industries LLC / Marine Bioproducts); Feb. 22, 2008 (1 page).
English Translation of Judge's Hand Written Records of Oral Hearing (1 page) [Apr. 9, 2008].

* cited by examiner

APPARATUS AND METHOD FOR HYDROLYSIS OF A PROTEIN CONTAINING RAW MATERIAL AND APPLICATION OF THE RESULTING HYDROLYSIS PRODUCTS

CROSS-REFERENCE TO RELATED APPLICATION

This application is a Divisional Application of U.S. patent application Ser. No. 10/725,039, filed Dec. 2, 2003, which claims priority to Danish Patent Application No. PA 2002 01859, filed Dec. 2, 2002, the complete disclosures of which are hereby expressly incorporated by reference.

BACKGROUND

This disclosure relates to plants and methods for hydrolysis of protein containing raw material, and to uses of the hydrolysis products obtained therefrom.

Various batch hydrolysis processes are known, each having certain disadvantages, such as prolonged processing time, low yields of soluble protein, deficient product quality or flavor, high fat content, and inefficient use of resources. This disclosure provides apparatuses, methods, and systems that provide hydrolysis of protein-containing material, such as fish, animal and plant materials, and hydrolysis products resulting therefrom.

SUMMARY

Provided herein are embodiments of apparatuses and methods that hydrolyze and separate a reaction mixture comprising (i) a protein-containing fish, animal or vegetable raw material and (ii) proteolytic enzyme. The raw material may be in the form of by-products or waste products from the processing of foodstuffs. The apparatuses and methods comprise an optional collection section or area, where the raw material (typically in pieces, such as fish or animal carcasses) is collected and optionally processed to reduce the size of the pieces of the raw material collected, a hydrolysis section or area that hydrolyzes the reaction mixture, an inactivation section or area that substantially inactivates the enzyme present in the reaction mixture, and a separation section or area where at least a portion of the reaction mixture is separated into at least one liquid component that comprises water soluble protein. In other embodiments, the water contained in the liquid portion comprising the water-soluble protein is evaporated to yield concentrated solutions comprising hydrolysate or dried to produce solid hydrolysate.

In other embodiments, the collection area and/or the hydrolysis area and/or the inactivation area and/or the separation area is capable of maintaining and does maintain the reaction mixture such that any emulsion present in the liquid component of the reaction mixture is below a predetermined level. In one embodiment, any emulsion present is at or below 5% of the reaction mixture, more preferably at or below 2%, even more preferably at or below 1% and most preferably at or below 0.5%. In another embodiment, any emulsion present in the reaction mixture is at or below 3%.

In some embodiments, the particle size of the raw material may be selected to reduce, minimize, or avoid emulsions from forming. For instance, in an embodiment of the invention where the raw material used comprises fish, the raw material may be loosely ground, chopped, or cut so that the size of the raw material pieces or particles is about 16 mm or greater in width. In one embodiment, the size of the raw material is from about 16 to about 50 mm in width, and in another embodiment the aggregate size of the raw material is about 30 mm or greater in width. Measurement of the size of a piece of raw material may be in any selected direction or dimension. Thus, a long strip or sheet of raw material that is 30 mm wide in only one direction may be acceptable for use with the present invention.

Skilled artisans would appreciate that the aggregate size of the raw material particle size may be achieved, controlled, or determined in several ways. For instance, processes used to grind raw material may have openings through which the raw material is forced to pass. The size and or shape of the openings thus can be varied accordingly to arrive at a desired aggregate size of raw material pieces. Similarly, chopping processes likewise may control how the raw material is cut or chopped. The size of the raw material pieces or particles may also be measured, such as by using a caliper or any other suitable measurement tool. Alternatively, the size of the raw material may be determined by correlating the weight of a piece of raw material to a size.

In some embodiments of the invention the use of larger sized raw material does not appreciably increase the time needed to hydrolyze the reaction mixture. For example, in one embodiment of the invention a 50% increase in the size of the raw material pieces may result in less than 10% of an increase in time needed to hydrolyze it in a reaction mixture, and more preferably results in less than a 5% increase in time.

In other embodiments, the apparatus is capable of hydrolyzing two tons, three tons, four tons, or five tons or more of raw material per hour. Apparatuses of the invention also may be capable of hydrolyzing even greater amount of raw material per hour, such as eight tons, 10 tons, 13 tons, or 15 tons or more of raw material per hour.

In addition to being capable of hydrolyzing a high capacity of raw material per hour, other embodiments of the invention are capable of operating at a desired capacity for extended periods of time. For example, in one embodiment an apparatus is capable of converting or transforming raw material into useful products continuously for at least about 72 hours. In another embodiment, an apparatus is capable of operating continuously for about 7 days or more. In yet another embodiment the apparatus is capable of operating continuously for about 2 weeks or more.

In another embodiment, the hydrolysis area or section comprises at least one hydrolysis reactor. The hydrolysis reactor may be substantially tube-shaped, although other shapes or configurations also may be used. In other embodiments, the hydrolysis area or section comprises a feeder screw for conveying a reaction mixture of enzyme and raw material through the hydrolysis area or section of the apparatus.

Feeder screws also may be used in other sections or areas of the apparatus, such as in the inactivation area or section described more fully below. For example, in one embodiment one or more feeder screws may be used for conveying the reaction mixture through the inactivation area. The feeder screw may remove reaction mixture comprising solid components, such as bones, and a liquid component for separation.

In another embodiment, the reaction mixture can include a fatty layer that can be separated, e.g., by pumping and/or decanting.

Yet other embodiments provide apparatuses and methods which provide yields of water-soluble protein of at least about 50%, 60% and 70% or more by weight based on the weight of protein in the raw material.

Yet other embodiments provide that the pH of the reaction mixture is not adjusted from its existing state. Yet another embodiment provides that the pH of the raw material is not adjusted or that the pH of the raw material and the pH of reaction mixture is not adjusted from its existing state. For example, the pH of the raw material and reaction mixture in such embodiments is between about 6 and about 9, preferably between about 6.5 and about 8 and more preferably between about 7 and 8 or about 7.

Yet other embodiments provide protein-containing products that comprise or contain amino acids derived from animal proteins, such as from fish. Other embodiments of the invention comprise providing protein-containing raw material from plants. Also disclosed are embodiments in which such products are used as food or as a nutritional supplement for humans or animals.

Other features and advantages of the embodiments of this disclosure will become apparent from consideration of the following description taken in conjunction with the accompanying drawings and claims.

BRIEF DESCRIPTION OF THE DRAWINGS

FIG. 1 is a block diagram according to one embodiment of an apparatus and process for hydrolyzing proteinaceous raw material, such as from animals, plants, or the like.

DETAILED DESCRIPTION

Figure 1:
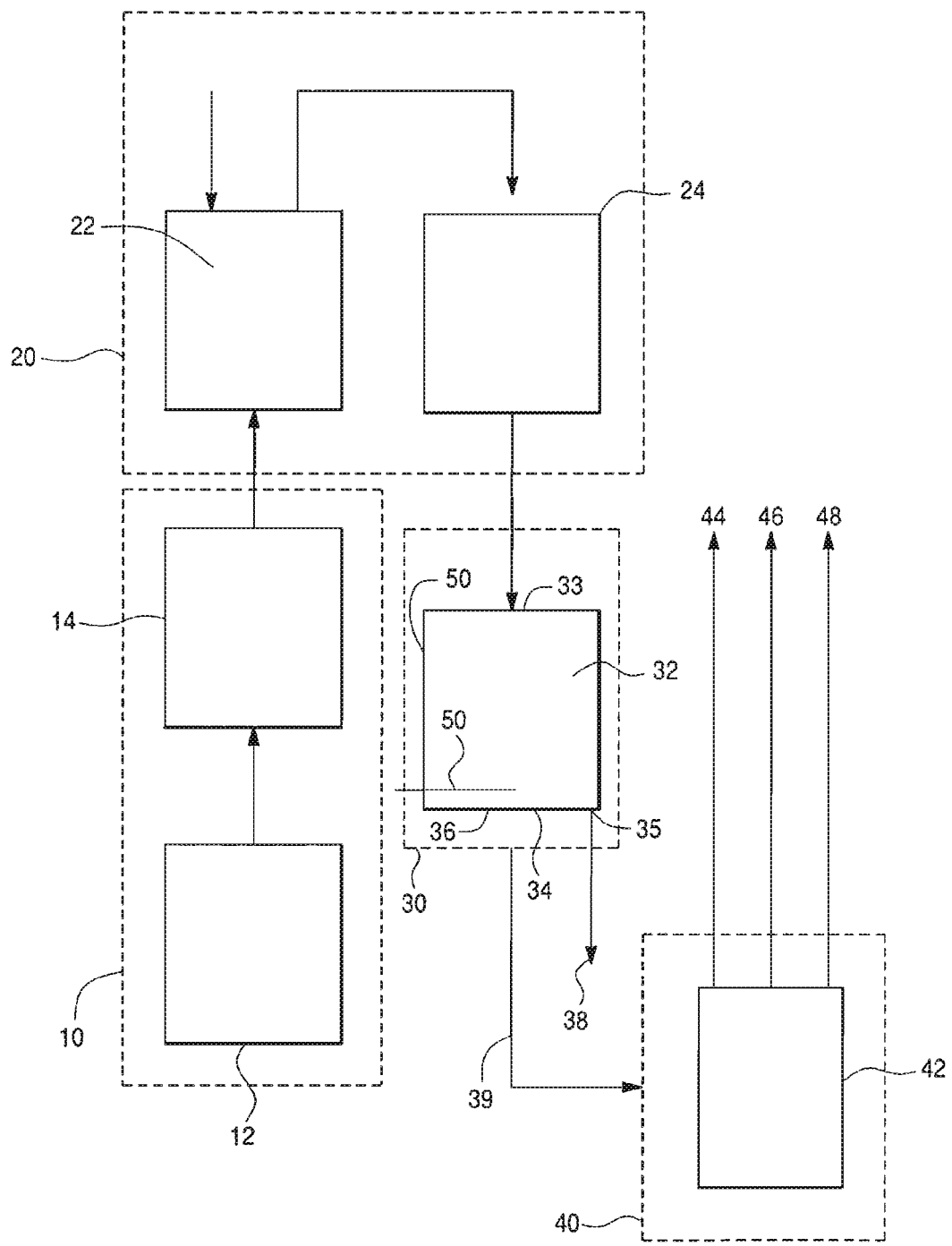

In this section, detailed discussion of various embodiments is provided. From the following discussion, skilled artisans readily will recognize numerous modifications, permutations and alterations that may be made to the various specific embodiments described.

A. RAW MATERIAL

The apparatuses, systems and methods described herein are useful for hydrolyzing proteinaceous (i.e., protein-containing) raw material into useful products, such as water-soluble proteins, peptides and amino acids. As used herein, the term "raw material" means any proteinaceous raw material from any one of or from several of the five kingdoms including plant, animal, protists, fungi, and bacteria, prior to the addition of enzymes that hydrolyze, convert, or transform the raw material into useful products. Thus, raw material may include, but is not limited to, non-enzyme-treated material derived from plants or animals, including fish, that are a source of protein, oil rich in unsaturated fatty acids, and bones.

Raw material derived from fish products and other marine organisms, such as crustaceans, poultry products, beef products and products of other ruminant animals, lamb products, swine products, and microbial products, such as blue-green algae, are well-suited for the purposes described herein. In the context of fish raw material, the raw material can, include, for example, bones, heads, tails, and viscera, as well as any other waste product produced from the processing of fish for human consumption. The raw material can also be, for example, slaughterhouse waste with meaty bones, or vegetable raw material.

In general, enzymes and water may be added to the raw material to form a reaction mixture that can hydrolyze the raw material under proper conditions. In one embodiment, apparatuses, systems and methods described herein are useful for processing raw material derived from or comprising fish to provide useful products that are oil rich in unsaturated fatty acids, such as omega-3 fatty acids, which have been shown to reduce the incidence of cardiovascular disease. In particular, raw material derived from fatty fish, including but not limited to mackerel, lake trout, herring, sardines, albacore tuna, and salmon, are high in two kinds of omega-3 fatty acids, eicosapentaenoic acid (EPA) and docosahexaenoic acid (DHA). When fatty fish are included in the raw material, the apparatuses, systems and methods described herein are capable of producing an oil component or phase that may be separated (e.g., by pumping out of the apparatus and/or decanting) and used to produce food additives containing omega-3 fatty acids, or further processed, e.g., to extract oil soluble vitamins.

In addition, fish is a source of the essential amino acids valine, leucine, isoleucine, lysine, methionine, threonine, tryptophan, and phenylalanine. In addition to the essential amino acids, hydrolysates described herein may also include significant levels of other amino acid-like compounds, such as taurine, which is used to absorb fats and fat-soluble vitamins. Taurine has been found to have many benefits, including reversing abnormal blood vessel response associated with cigarette smoking. Thus, the hydrolysates described herein can be used to produce taurine tablets or other taurine-containing products. Preferably, the taurine tablets or other taurine-containing products are suitable for human consumption. As used herein, the term "hydrolysates" refers to water-soluble proteins, peptides and amino acids.

In addition, taurine is an essential nutrient for cats because, unlike dogs and humans, for example, cats cannot synthesize their required amount of taurine to meet their needs. In contrast, taurine can be produced from the essential amino acids methionine and cysteine in humans and dogs. Cats, however, lack the enzyme for this reaction, so taurine must be obtained from food. Accordingly, the hydrolysates described herein can also be used to make food additives for cats.

B. THE COLLECTION AREA

The apparatuses, systems or methods of this disclosure can include one or more collection or preparation areas. The collection or preparation area simply connotes a place, e.g., an assembly, section, stage or separate housing, chamber, reactor or unit, where raw material can be collected, and optionally further processed, prior to being subjected to hydrolysis. The collection area can be in direct or indirect communication with the hydrolysis area, and located either nearby or remote from the hydrolysis area. Thus, the collection area can be directly connected to the hydrolysis area, or connected through one or more intermediate sections, connections or conduits. Alternatively, the collection area can be remotely located from the hydrolysis section, e.g., at a fish processing plant or animal slaughterhouse, and the raw material, with or without processing on-site, may be simply transported and supplied to the hydrolysis area, with or without further processing there.

The collection area thus can include pre-hydrolysis processing steps, such as mincing, grinding, chopping, cutting, blending or other mechanical actions that result in size reduction of the raw material pieces, thereby resulting in a greater effective surface area of the raw material to allow more effective contact between the raw material pieces and the one or more enzymes. In addition, the raw material pieces have dimensions that avoid or minimize emulsification when conveyed through the hydrolysis area, as described below. Raw material having a high fat content, such as a fat content of about 10% w.w. (wet weight) or more, and more preferably 15% or more, may be processed into larger sized pieces in order to help reduce, minimize, or avoid emulsification. For example, raw material pieces may have dimensions from about 15 mm to about 50 mm, preferably from about 20 mm to about 40 mm and from about 25 mm to about 35 mm in at least one direction or dimension. In other embodiments, even larger raw material pieces may be utilized and it surprisingly has been found that pieces of up to 300 mm in length or more, such as whole fish backbones, can be processed without significantly extending or increasing the time it takes to hydrolyze the raw material. In certain cases, whole fish and other similarly-sized raw material pieces may be utilized.

Alternatively, smaller sized raw material may be used in some embodiments, such as when the raw material has a low fat content that presents a lower likelihood of emulsification than higher fat content material. Thus, in some embodiments the size of the raw material pieces may be smaller than 15 mm. For purposes of this aspect of the invention, a low fat content raw material has a fat content of about 5% w.w. or less, and more preferably is about 2% w.w. or less.

The process of collection, including optional pre-hydrolysis processing, can be adjusted or varied to control the amount of emulsification of any liquid present in the raw material as a result of pre-hydrolysis processing. Emulsification can be controlled, for example, by minimizing vigorous or turbulent mixing or processing or by utilizing larger pieces of raw material to reduce emulsification from fine grinding or mincing. In addition, chemical demulsification agents or additives may be used to decrease, prevent, or eliminate emulsification. Chemical demulsification may include the addition of one or more chemical demulsifying agents or additives to the raw material or reaction mixture in order to enhance phase separation. If chemical emulsion control agents or demulsifiers are used, they should be chosen to minimize emulsion or other effects in the desired final products.

Emulsion control also can include, alternatively or in addition, demulsification by known physical means. For example, physical demulsification may include gravity settling and/or electrostatic coalescence. The principal idea behind the later method is to enhance phase separation through electrically-aided charging, migration, collision, and thus coalescence of dispersed phase droplets within the system.

In various embodiments, water may be added to the raw material in the collection area. If the temperature of the raw material is low (e.g., if it is frozen or refrigerated) the water may be heated in order to bring the temperature of the raw material or reaction mixture to a desired temperature or temperature range that is more conducive or suitable for hydrolysis. For example, the temperature of the reaction mixture may be between about 20° C. to about 85° C. after the addition of water and enzyme to the raw material. Preferably, the reaction mixture temperature is between about 30° C. and about 70° C., and more preferably is from about 50° C. to about 60° C. after the addition of water and enzyme to the raw material.

Enzymes also may be added to the raw material in the collection area. As discussed below, water and/or enzymes alternatively or additionally may be added to the raw material after being introduced into the hydrolysis area. The addition of enzymes and water to the raw material in the collection area may allow the hydrolysis process to begin. Likewise, the temperature or other conditions of the reaction mixture may be controlled so as to control or limit the extent of hydrolysis that takes place prior to introducing the reaction mixture to the hydrolysis area. Controlling the hydrolysis process may permit the addition of enzymes and/or water when it is convenient or desired while minimizing, reducing, or avoiding altogether the possibility of emulsification during handling, transport, or storage of the reaction mixture prior to introducing it into a hydrolysis area.

C. THE HYDROLYSIS AREA

The apparatuses and methods of this disclosure can also include one or more hydrolysis areas that receive raw material from the optional collection area. The hydrolysis area simply connotes the place, e.g., an assembly, section, stage, separate or connected housing, chamber, reactor or unit, where the raw material may be subjected to hydrolysis. Thus, the hydrolysis area is typically located after the collection area (if one is provided).

As discussed above, the hydrolysis area may be located either nearby or remotely from the collection area. In addition, a collection area and hydrolysis area may be integrally connected to each other so that raw material or reaction mixture may be found in either area. Thus, a collection area and hydrolysis area may be in fluid communication with each other or alternatively may be identified by substantially the same equipment or components in an apparatus, system, or method of the present invention. For example, a container or supply system having raw material may also be a hydrolysis area after the addition of enzymes and water.

One or more enzymes may already be mixed with the raw material prior to entry into the hydrolysis area, may be added to the raw material in the hydrolysis area, or both. The addition of one or more enzymes, and optionally water, to the raw material forms a reaction mixture, i.e., reaction mixture is different from the raw material in that the reaction mixture additionally comprises one or more enzymes. Likewise, water, including water optionally heated to between about 20° C. to about 85° C., may be added to the raw material before and/or during residence in the hydrolysis area. As discussed above, the temperature of the water and/or raw material may be adjusted to other temperature ranges that likewise may be suitable for hydrolysis to occur. Whatever the sequence of admixture, the raw material and enzyme are contacted and present together as a reaction mixture in the hydrolysis area.

In another embodiment, one or more enzymes also may be added to the raw material by siphoning or re-circulating a liquid portion of the reaction mixture having active enzyme from a first location of the hydrolysis area to a second location. For example, the liquid portion of the reaction mixture may be recirculated from near the exit end of the hydrolysis area by reintroducing such liquid portion into or near the entry end of the hydrolysis area.

Alternatively, liquid from the hydrolysis area may be siphoned or re-circulated into a collection area in order to help initiate hydrolysis, to help thaw or warm the raw material, or both. Typically, enzymes that are contacted with the raw material and facilitate hydrolysis are not consumed in the hydrolysis, or at least may be reused several times before the enzyme becomes unable to hydrolyze raw material. Accordingly, such enzymes that are already utilized in the hydrolysis of raw material retain its activity and thus are a viable source of active enzymes.

Re-circulating an enzyme can be at least a partial or complete substitute for adding new enzyme, i.e., the re-circulated enzyme can be introduced into the hydrolysis area or the collection area prior to conveyance to the hydrolysis area as a substitute for or in addition to new enzyme. For instance, in one embodiment of the invention, about 30% or more of the enzyme in a hydrolysis area is re-circulated and reused. Even higher amounts of enzymes may be re-circulated or reused, such as about 50% or more, or 80% or more of the enzyme in the hydrolysis area.

Under suitable conditions, one or more enzymes may react with the raw material to yield a hydrolysate or hydrolysis product, as well as other soluble or insoluble products. As used herein, the terms "hydrolysate" and "hydrolysis product" may be used interchangeably and refer to soluble proteins, peptides and/or amino acids in water. As discussed above, the reaction mixture is deemed to include the entire contents of the hydrolysis area including raw material, enzyme, other constituents, such as water, hydrolysis product so formed, and solids, such as bones that are left following hydrolysis. The hydrolysis area forms an environment that facilitates hydrolysis, and according to one embodiment substantially controls emulsification of the reaction mixture to predetermined levels while hydrolyzing the reaction mixture. Emulsion control and/or demulsification can be effected substantially as described above.

The hydrolysis area can include various configurations and devices to chemically and/or physically aid in hydrolyzing the reaction mixture. The hydrolysis area also can include various configurations and devices to aid in moving, conveying, or transporting the reaction mixture through the hydrolysis area. In one embodiment consistent with a continuous process, reaction mixture can be advanced through a hydrolysis area toward an inactivation area by a transport mechanism and/or provide gentle agitation and/or mixing, e.g., conveyor belts, vibration belts, microwave or ultrasound transmission systems, tumblers, and the like, while avoiding or minimizing the formation of an emulsion.

Figure 7A:
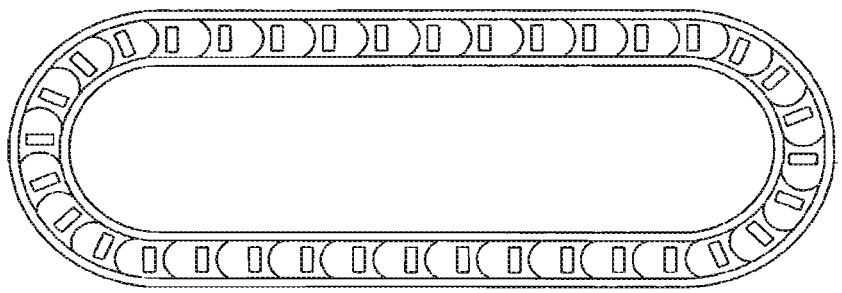
FIG. 7 illustrates alternative configurations and devices to aid in moving, conveying, or transporting raw material or a reaction mixture.

For example, the hydrolysis area may utilize an Archimedes screw, single or twin screw pumps, or the like. Thus, an auger may turn within a housing to move and/or gently mix the reaction mixture. Likewise, a hydrolysis area may have a housing or sleeve with an internal surface defining a passageway through which the reaction mixture travels. Rather than using an auger to move and/or gently mix the reaction mixture, however, the internal surface of the housing may have a threaded channel that accomplishes similar movement and/or gentle mixing of the reaction mixture by rotating the housing. This alternative embodiment, which is illustrated in FIG. 7A, thereby accomplishes a similar result as a screw pump without an internal moving part.

Figure 7B:
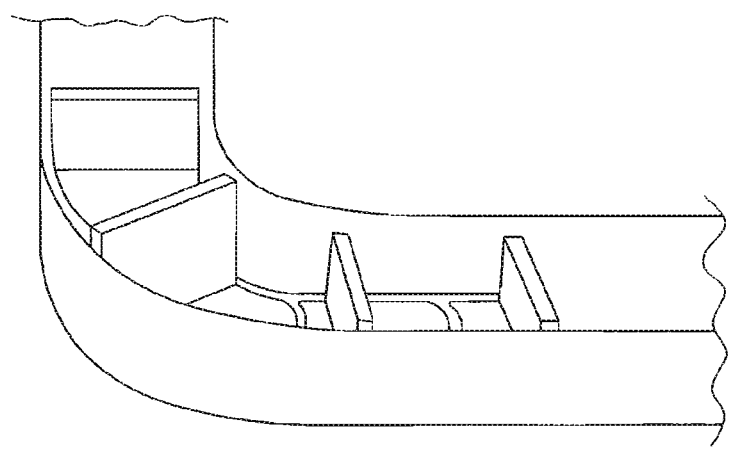
Figure 7C:
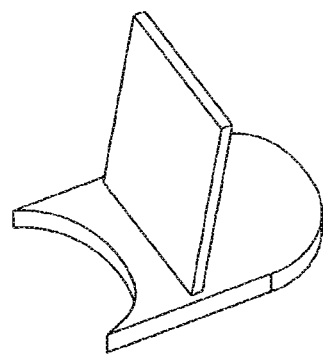
Figure 7D:
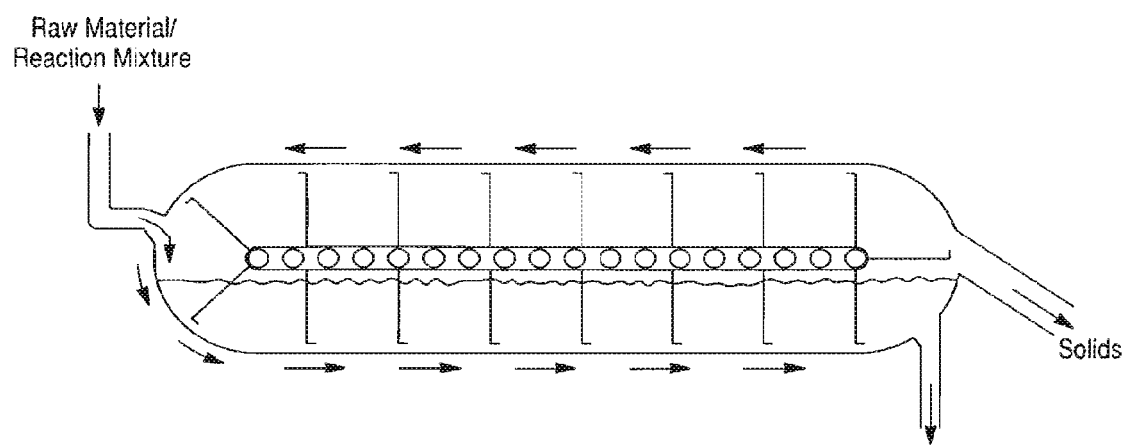

In another embodiment, shown in FIG. 7B, a loop of a bath, housing, or channel may be used for a hydrolysis area. In this embodiment, a bath or channel of reaction mixture is provided with moving screens, panels, containers, or the like moving therein. Raw material or reaction mixture may be introduced at a first location of the loop and is moved through at least a portion of the loop by the screens, panels or containers. Optionally, water and/or enzymes also may be added at this or another location in the hydrolysis area. The hydrolyzed components and solid remains may be removed from the hydrolysis area at a second location.

As described above, the reaction mixture can be moved by means of one or more feeder screws or the like that advance the reaction mixture while mixing it in a controlled fashion to promote or optimize contact between enzyme and raw material, and also while avoiding or minimizing emulsion formation. For example, the feeder screws can rotate clockwise in a predetermined first period of time or until certain parameters are met, and counter-clockwise in a predetermined second period of time or until other parameters are met, to mildly agitate the reaction mixture.

The rate and period of time for the clockwise and counter-clockwise rotation may each be independently varied. For example, a time period for clockwise rotation may be longer, equal to, or shorter than the time period of time for counter-clockwise rotation. Typically, the time period for clockwise movement may be from about 120 seconds to about 30 seconds, and more preferably about 90 seconds, while the time period for clockwise movement may be from about 90 seconds to about 30 seconds and more preferable about 60 seconds. Rates of clockwise and counter-clockwise rotation may be, for example, from about 3 revolutions per minute ("rpm") to about 0.10 rpm, and more preferably from about 0.5 rpm to 0.75 rpm or about 0.66 rpm. The screws can continuously or intermittently provide such clockwise and counter-clockwise rotations. In these embodiments, the holding times in the hydrolysis section of the inactivation reactor may, therefore, be controlled by first allowing the feeder screws to alternately rotate in one direction and the other, in order thereby to transport reaction mixture in a step-by-step movement where the reaction mixture is carried slightly longer forwards than it is pulled back.

The material is contacted with one or more enzymes, i.e., the reaction mixture is allowed to react, in the hydrolysis area for a total period of time from about 120 minutes to about 15 minutes, preferably from about 90 minutes to about 30 minutes, and most preferably from about 45 minutes to about 50 minutes. Thus, the rotation rates, rotation time periods and conveyance lengths of the raw material through the hydrolysis area may be routinely determined by the skilled artisan to obtain the desired residence time of the reaction mixture in the hydrolysis area.

D. THE INACTIVATION AREA

The apparatuses or methods of this disclosure can include one or more inactivation areas. The inactivation area simply connotes the place, e.g., an assembly, section, stage or separate housing, chamber, reactor or unit, where the enzyme in the reaction mixture is inactivated following hydrolysis. Inactivation can be carried out using various methods, such as increasing the temperature of the reaction mixture to denature the enzyme, thus substantially inactivating it, or by modifying the pH of the reaction mixture. As used herein, the phrase "substantially inactivating" means, for example, rendering the one or more enzymes that have already been contacted with raw material to be greater than about 90% inactive, preferably greater than about 95% inactive, and more preferably from about 99% inactive.

When heating is used to inactivate, care should be taken that the resulting end products do not lose their nutritional value, i.e., decompose or destroy the proteins, peptides and amino acids in the reaction mixture. Thus, the inactivation area should be adjusted to maintain a temperature sufficient to inactivate the hydrolysis enzyme, for example, of above about 85° C. to about 100° C., preferably about 90° C. to about 95° C. The heating temperatures to inactivate the one or more enzymes can be maintained from about 0.5 minutes to about 45 minutes, more preferably from about 1 minute to about 30 minutes, even more preferably from about 5 minutes to about 25 minutes, and most preferably from about 10 minutes to about 20 minutes. For example, an 85° C. to about 90° C. temperature may be maintained for about 15 minutes to inactivate the enzymes. Inactivating the enzymes by adjusting the temperature of the solution is efficient because it also results in a raised temperature range which is desirable, for example, for the decanter or tricanter separation (or other separation) as described herein.

In another embodiment, one or more acids or bases are added to the reaction mixture to adjust the pH to substantially inactivate the one or more enzymes. Typically, the enzymes used in this process are inactivated when the reaction mixture has a pH of less than about 4 and greater than about 9.

In another embodiment, the pH range is not adjusted. This is advantageous because it eliminates the need for acidic or basic solvents which present, for example, environmental concerns regarding their use and disposal. Also such solvents can be costly. In this embodiment, where the pH is not adjusted, enzymes having optimal activity in the following pH ranges may be used: having an optimal range pH of between about 6 and about 9, preferably between about 6.5 and about 8 and more preferably between about 7 and 8 or about 7.

The inactivation area can comprise a reactor or chamber having a single inlet and single outlet for the reaction mixture, or it can be an apparatus that includes one or more separate inlets and one or more separate outlets that is capable of facilitating a continuous hydrolysis process. The inactivation area may be designed to permit either batch or continuous inactivation reaction, or both.

According to one embodiment, discussed in further detail below, an exit end of an inactivation reactor, i.e., where the inactivated reaction mixture exits the inactivation area, has at least one outlet for a solid matter constituent, phase or component (such terms being used to describe the part of the reaction mixture that comprises solids) of the inactivated reaction mixture and at least one outlet for a liquid constituent, phase or component (such terms being used to describe the part of the reaction mixture that comprises liquid) of the inactivated reaction mixture, positioned at a distance from the outlet for the solid matter component. The outlet for the solid component is positioned at a distance from the outlet for the liquid component to sufficiently avoid or minimize mixing of the solid components with the liquid-only components. Accordingly, in one embodiment, a continuous enzymatic hydrolysis of a raw material, such as meaty broken bones, may be carried out. In such cases, solid matter, which may chiefly consist of cleansed bones, can soon accumulate at the bottom of the inactivation area, and the fatty fraction of the liquid phase will gather at the top of the inactivation reactor.

Depending upon the temperature at which the inactivation area is operated, the exposure of the fatty fraction liquid phase and/or solid matter to the heated walls of the inactivation area may cause deposits or residue to form on the inner surface of the inactivation area. Over time, these residues and deposits may increase, and thereby requiring additional heat to be provided to the inactivation area in order to maintain a desired temperature to inactivate the enzymes. Eventually, the inactivation area may be shut down so that the inner surface can be cleaned to remove excess residue and deposits. In one embodiment a wiper, blade, or the like may be used to periodically skim or clean the inner surface of the inactivation area, thereby allowing it to remain in service for a longer period between shut-down and cleaning. Alternatively, a gentle mixer or stirrer may be used to create fluid flow of reaction mixture that contacts heated surfaces of the inactivation area.

If an auger or screw is provided in the inactivation area, one alternative embodiment provides that the auger or screw may be heated so that heat is distributed more evenly or efficiently into the reaction mixture. In this embodiment, the overall operating temperature of the heated surfaces may be lowered from the ranges provided above by about 3° C. or more, or more preferably by about 5° C. or more. Lowering the temperature of the heated surfaces may reduce or eliminate the build up of deposits or residue because of better or more efficient distribution of heat to the reaction mixture.

In one embodiment, the inactivation reactor at its exit end comprises at least one outlet for the separate removal of the solid matter component, such as bones and the like, to the extent necessary and at the desired rate. The removal of the solid matter component may be continuous or intermittent and advantageously avoids the accumulation of a voluminous solid matter that unnecessarily takes up space in the inactivation area, thereby preventing or delaying the additional or continuous feeding of new reaction mixture at the entry end of the inactivation area. The at least one outlet for the solid matter component may be substantially positioned at the same level or below the level of the solid matter layer where it is located in the inactivation area, or may simply comprise a transporter (e.g., screw, conveyor, belt, etc.) for the bones and other solid components that are located at the bottom of the inactivation area.

In one advantageous embodiment, a single screw is employed in the inactivation chamber. At the exit end of the chamber, there is provided an opening where the inactivated reaction mixture (solid component and liquid component) is emptied through a tube, passage or conduit by means of a large, slow-turning pump that avoids or minimizes emulsion (e.g., an Archimedes pump, a single or double screw pump, or the like), onto one or more screens/filters which substantially removes the larger pieces in the solid component (e.g., bone) above a predetermined filter mesh size.

As used herein, "mesh size" refers to, for example, the number of holes per square inch in a screen. In embodiments where more than one filter or screen is utilized, each filter or screen may have varying mesh sizes so that, for example, the first filter or screen that contacts the inactivated reaction mixture has the largest mesh size, and the mesh size gradually decreases in each subsequent filter or mesh that the reaction mixture contacts. Such variance in mesh size in this multiple filter or screen configuration ensures that the largest solids are separated early on while the smaller mesh size filters or screens effectively separate the smaller-sized solids. Typically, the mesh size is from about 1 to about 200 mesh, where particles pass through a screen having between 1 hole and 200 holes per square inch. Also encompassed are screens having mesh sizes from about 5 mesh to about 150 mesh, from about 20 mesh to about 100 mesh and from about 30 mesh to about 80 mesh.

The liquid phase, including soluble and insoluble particulates, that passes through the filter or screen is pumped to a liquid separator, such as a tricanter (also called a three phase separator), which facilitates the separation of a fat or lipid component, an aqueous component comprising dissolved proteins, peptides and amino acids, and an aqueous component comprising undissolved proteins, peptides and amino acids. The pump preferably used in this embodiment is a high capacity pump with slow moving parts in order to avoid creating emulsions. However, only a fixed volume goes to the tricanter so that any volume in excess of the fixed volume is returned to the inactivation area (e.g., via an overflow return). Typically, the fixed volume of the tricanter is determined by the maximum volume of liquid the tricanter can hold.

When the inactivation reactor has at least one or more additional outlets for the removal of the liquid phase, positioned at a distance from the outlet for the solid matter phase, the liquid component may advantageously be discharged freely, independently of how and when and in what quantity the solid matter phase is discharged. As described above, the distance between the outlet for the one or more additional liquid component and the outlet for the solid component is sufficient to avoid or minimize mixing of the solid components with the liquid-only components.

In other embodiments, the inactivation area can be provided with one or more feeder screws for the purpose of shifting or conveying the solid matter component and/or the liquid component, respectively, through the inactivation area in the direction of the respective outlets. This ensures in a simple manner that the reaction mixture (now comprising primarily solid matter, and liquid, which comprises hydrolysis product) does not accumulate in the inactivation reactor and prevent addition of new reaction mixture for inactivation.

Figure 8A:
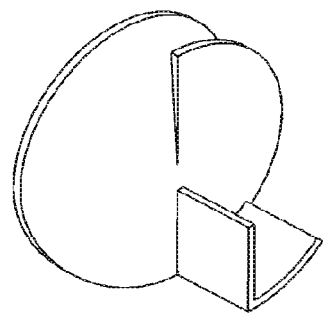
FIG. 8 is a partial view of a portion of a screw or auger having a scoop, spatula, ledge, or sheet arranged along the periphery of the thread.
Figure 8B:
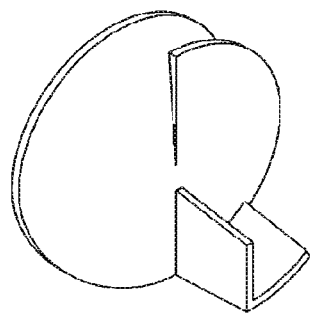

In addition, any of the feeder screws described herein can be fitted with scoops, spatulas, ledges, or sheets arranged along the periphery of the threads in order thereby to ensure reliable transport or conveyance of raw material, reaction mixture or inactivated reaction mixture in the respective areas (i.e., the collection area, the hydrolysis area, the inactivation area and the separation area). One illustration of a feeder screw having this configuration is provided in FIG. 8. As shown, a scoop, spatula, ledge, or sheet may be disposed at or near the outermost edge of the screw or auger. As the screw or auger rotates, these devices gently slide under solid matter resting on the bottom surface or floor and gently lifts the solid matter. As the screw or auger continues to rotate or turn, eventually the solid matter slides and falls off of the scoop, spatula, ledge or sheet. In this manner, the screw or auger can provide gentle mixing of solid matter that might otherwise entrap portions of the reaction mixture that could be hydrolyzed.

And as described above for the collection and hydrolysis areas, the inactivation area may be designed to maintain a low level of emulsion in the reaction mixture. For example, the inactivation area may comprise a conveyance mechanism (e.g., screw or paddle or spatula) that conveys the inactivated reaction mixture at a rate that avoids or minimizes emulsification. Emulsion control or maintenance and/or demulsification can be achieved by the methods described above for the collection and/or hydrolysis areas. Where screws or other devices are used to transport and mix the reaction mixture in the inactivation section, such devices may be configured to avoid vigorous mixing that can result in additional emulsification.

E. THE SEPARATION AREA

The apparatuses or methods of this disclosure can include one or more separation areas. The separation area simply connotes the place, e.g., an assembly, section, stage or separate housing, chamber, reactor or unit, where the inactivated reaction mixture is separated into its constituent components after inactivation in the inactivation area. The separation area can be in direct or indirect communication with the inactivation area, and located either nearby or remote from the inactivation area. Thus, the separation area can be directly connected, or connected through one or more intermediate sections, connections or conduits. Alternatively, the separation area can be remotely located from the inactivation area and the inactivated reaction mixture simply transported to the separation area.

The separation area is capable of separating at least a portion of the inactivated reaction mixture into two or more constituent components using any number of separation means or systems, as discussed below. Separation can be conducted in sequence, e.g., first solids may be separated from the liquid, and then the different components of the solid and/or liquid may be separated. Combinations of separation procedures likely will be employed (e.g., pumping off of the fatty layer, screen filter separation of liquid from solids, and centrifugation, decanting and/or tricanting) may be used to achieve the desired separation and products. Separation also can be conducted in parallel or concurrently, e.g., solids and liquids can be separated off from the reaction mixture at the same time, and then further separated. Different liquids, including e.g., the fat layer, the aqueous layer comprising dissolved proteins, peptides and amino acids, and the aqueous layer comprising undissolved proteins peptides and amino acids can be removed or separated by, for example, pumping, centrifugation, decanting, tricanting or any combination thereof concurrently and/or sequentially.

In one embodiment, separate outlets for different components of the reaction mixture are found in the separation area. One or more outlets may be present in the separation area to remove the solid component and may be subjected to further processing as described herein, for example, processing the solid component into bone meal. One or more outlets may be present in the separation area to remove the liquid component, which may be further separated into the various fractions of the liquid component, such as a fat or lipid component, an aqueous component comprising dissolved proteins, peptides and amino acids, and an aqueous component comprising undissolved proteins, peptides and amino acids. For example, the outlet for one or more liquid components may appropriately be positioned in a plane, which is parallel to and intersecting the respective liquid component and at a distance from the outlet for the solid matter phase sufficient to avoid or minimize mixing of the solid component with the liquid component. Thus, for example, a solid matter phase is discharged from one outlet into a container or chamber in the separation area that receives the solid matter, while a liquid component is discharged from another outlet spaced apart from the outlet for the solid matter.

In another embodiment, a filter or screen, as described above, is employed to filter the reaction mixture and separate, for example, solid component from liquid component. In such embodiments, reaction mixture comprising both a solid component and a liquid component are contacted with the filter screen and the solids taken off above the filter and liquid filtrate taken off below.

In yet another embodiment, the solid component of the inactivated reaction mixture can be separated from the liquid component by any of the methods described above or by other filtration methods. Meanwhile, the liquid component can be pumped, flushed, spilled, piped, or otherwise transported to one or more decanter or tricanter centrifuges, which spins or otherwise separates the liquid component into separate constituent components (i.e., fat or lipid component) and/or aqueous component comprising dissolved proteins, peptides and amino acids, and/or aqueous component comprising undissolved proteins, peptides and amino acids.

F. BATCH AND CONTINUOUS OPERATION

The apparatuses and methods described herein, or areas thereof, may be used in batch process mode. In a batch process, a predetermined amount of raw material is fed through the system and processed before any additional raw material is fed into the system. Embodiments disclosed herein are, with appropriate scale-up, capable of hydrolyzing two tons, three tons, four tons, or five tons or more of raw material per hour.

Advantageously, however, the apparatuses and methods involve a continuous process, in which raw material is continuously fed without any need for pre-measurement, and the process runs continuously for periods of up to 1-3 months or longer. Thus, any of the aforementioned areas, apparatus, methods or plants may be configured to continuously operate 24 hours a day for days or weeks at a time without interruptions. Advantageously, the apparatuses and methods are configured to provide at least three days of continuous operation, more advantageously at least seven days, and more advantageously at least ten to thirty days of continuous operation. At some point, the operator may find it desirable to stop production and clean the various areas to maximize the efficiency and capabilities of the system. For example, cleaning the various areas include chemical and/or physical means, such as scooping or scraping solid matter or residue from the bottom or side walls of each respective area, addition of acid or base to dissolve solid matter or residue, and application of pressurized liquid or solvent to remove solid matter or residue.

In any of the embodiment described herein, an apparatus or method may comprise more than one area or section performing a similar or the same function in parallel. For example, two or more inactivation areas may be provided with an apparatus or method so that the apparatus may continue to operate even if one of the inactivation areas is shut down for maintenance or cleaning. Likewise, multiple areas or sections may be used to provide greater adjustability of processing rates under optimum conditions. For instance, two or more smaller tricanters may be used to separate components more efficiently and/or more quickly than a single, large tricanter. Thus, an apparatus or method that is capable of processing 10 tons or more of raw material per hour may have two or more tricanters capable of processing 5 tons each.

Alternatively, an apparatus or method of the present invention may combine two, three or more areas or sections within a single housing or assembly. For example, an extended, rotating auger or screw can be provided within a housing or chamber. As the screw or auger rotates, it advances the raw material or reaction mixture through the housing or chamber. Different regions of the housing may have different operating conditions corresponding to the area, section, or stage of the hydrolyzing processes described above. Thus, an initial portion or region of the housing may be designated as a hydrolysis area having a temperature within a range that is conducive for hydrolysis. A second portion or region of the housing may be an inactivation area having an elevated temperature that inactivates the enzyme. A third portion or region of the housing may be at least a portion of a separation area where the inactivated reaction mixture is separated into its constituent components. For instance, a portion of the housing may form a screen or plurality of apertures through which the liquid phase may pass. Continued turning of the screw thereafter urges solid matter toward a collection point or subsequent processing area.

G. EMULSION CONTROL

As mentioned above, under certain circumstances, such as when low fat content is important for the end product or when high quality oils are desired, it is desirable to keep as much of the fat component as possible substantially separated from the aqueous component. For example, the fat component may be removed during the process, such as after inactivation as described above. Alternatively, the fat component may be removed prior to inactivation and, if so, is preferably removed and substantially free (i.e., less than 90%, preferably less than 95%, more preferably less than 99%) of the aqueous phase that contains active enzyme. In another embodiment, the amount of emulsification may be controlled in the reaction mixture by methods known by one of ordinary skill in the art. Emulsification causes protein and lipid to bind together, and it has been found that, once mixed in the form of an emulsion, it is difficult to later separate the protein and lipid components using centrifugation in a large scale process. Thus, when the process causes emulsification due to blending, high sheer forces, or by some other means, it is difficult to obtain an end product having a fat or lipid content below 2-3% from starting raw material that has a fat content of 15-25% w.w., as do most raw fish, poultry and meat products that have not been pre-processed for fat reduction. It has been found, rather, that yields containing less than 1% fat in dry matter (2-3% fat) from starting raw material containing 15-25% fat are possible in a large scale process if the reaction mixture is conveyed in a manner that controls or limits emulsification to an amount below 10% of the reaction mixture, more preferably below 5% of the reaction mixture, more preferably below 2% of the reaction mixture, more preferably below 1% of the reaction mixture, and most preferably at or below 0.5% of the reaction mixture.

Such emulsion control can be accomplished in various ways, such as by minimization of vigorous mixing and turbulence, as discussed above. Additionally, or alternatively, chemical emulsion control agents and/or physical or chemical demulsification may be utilized.

The percentage of emulsification in the reaction mixture can be measured, for example, by taking a representative sample from the hydrolysis reactor and/or from the inactivation reactor and comparing the volume of emulsion with the total volume of the reaction mixture or inactivated reaction mixture. The solid matter component is removed from the representative sample, and the liquid portion it is centrifuged for a time and spin rate sufficient to separate the fat or lipid component from the remaining aqueous component(s). Centrifugation times can vary from about 30 seconds to about 30 minutes, preferably from about 1 minute to about 15 minutes, more preferably from about 2 minutes to about 10 minutes, and most preferably from about 3 minutes to about 5 minutes. Again, as described above, all range limits disclosed herein may be interchanged to form new ranges. For example, centrifugation times of between about 30 seconds and 1.0 minutes, 1 minute to about 3 minutes, and 5 minutes to about 15 minutes are also encompassed. Centrifugation spin rates vary from about 500 rpm to about 10,000 rpm, preferably from about 1000 rpm to about 5,000 rpm, more preferably from about 2,000 rpm to about 4,000 rpm and most preferably about 2,500 rpm to about 3,500 rpm. The centrifuge tube is then removed from the centrifuge and the contents are analyzed. The centrifuge tube can contain a sediment component or portion of insoluble or undissolved proteins, peptides and amino acids, an aqueous component or portion above the sediment portion having dissolved proteins, peptides and amino acids, an oil or fat component or portion above the aqueous component, and an emulsified component or portion, which comprises an suspension of oil or fat in water, separating the oil portion from the aqueous portion. The percentage volume of the emulsion portion versus the combined sediment, aqueous and oil portions represents the percentage by volume of emulsion in the reaction mixture.

H. THE REACTION MIXTURE AND RESULTING HYDROLYSATE

As mentioned above, the reaction mixture includes protein-containing raw material, enzyme, and water. When certain raw material, such as fish and bone-containing meat, is used, the reaction mixture includes at least a solid matter component and at least one liquid component. If the raw material further contains fat, the liquid in the reaction mixture typically separates into several distinct components, including, but not limited to, a fat or lipid liquid component and at least one liquid aqueous component. Thus, the reaction mixture can separate into several distinct components including one or more of a solid component, at least one aqueous liquid component, and fat-containing liquid component.

When fat or lipids are present, it may stratify on top of the aqueous liquid. Thus, a substantial amount of the fat component can settle at the top of the inactivation area or hydrolysis area and may, if so desired, be removed or separated through an outlet for the fat component at the exit end of the inactivation area or hydrolysis area that is positioned in a plane parallel to and intersecting the fat component. Alternatively, the fat or lipid component may be removed or separated by pumping through one or more conduits present in the hydrolysis area, inactivation area and/or separation area, where it may be further separated by centrifugation and/or decanting, as described herein. Additionally, or in the alternative, the fat or lipid component can be removed with the aqueous component and separated by centrifugation and/or decanting.

The aqueous liquid component, which can contain partly dissolved amino acids; peptides and/or proteins, and partly non-dissolved or insoluble amino acids, peptides and/or proteins, or mixtures of these ingredients, as well as fat droplets, may also be independently removed or separated through one or more similarly arranged aqueous component outlet at the exit end of the inactivation area and/or separation. Alternatively, the aqueous liquid component may be removed or separated by pumping through one or more conduits present in the inactivation area and/or separation area.

The liquid component also may include non-dissolvable and non-dissolved ingredients, which may exist in a second separate aqueous component, typically found in a layer below the aqueous layer containing the soluble components. Like the other liquid components, this second aqueous component may be removed or separated through one or more separate outlets at the exit end of the inactivation area where the outlets are positioned to contact the second aqueous component, or alternatively pumped out through one or more conduits in contact with the second aqueous component.

I. PRODUCTS PRODUCED

The reaction mixture, including the solid and liquid components, can be extracted and/or separated to yield different useful products using the apparatus and methods described herein. The fat component can be extracted and processed into various useful products, such as, but not limited to, food additives and other edible oils. The solid matter component can also be extracted and processed into various useful products such as, but not limited to, bone meal and fertilizer. The liquid component can be further separated into various fractions, including but not limited to a fat or lipid component, an aqueous component containing water soluble proteins, peptides and amino acids, and an aqueous component containing water insoluble and undissolved proteins, peptides and amino acids. The hydrolysate comprising the water soluble protein can, depending on the raw material, be high in protein content, low in fat content, and have a high digestibility coefficient, which can make it useful in industrial fermentation, or as food additive, nutritional supplement, broth, biological culture medium, or fertilizer, among other things.

The coefficient of digestibility or digestibility coefficient can be measured in different animals, such as humans, dogs, cats, mink, etc. The digestibility coefficient refers to the proportion of ingested hydrolysate product that is actually digested and absorbed to serve the metabolic needs of the animal. In one embodiment, digestibility is measured in mink. Typically, mink are fed a known amount of hydrolysate that is extracted from the water-soluble protein fraction, and their waste product is analyzed and measured for protein content. The amount of protein absent from the waste product is assumed to have been absorbed to serve the metabolic needs of the animal.

Advantageously, the hydrolysate has a digestibility coefficient of at least about 70%, preferably at least about 80%, more preferably at least about 90%, even more preferably at least about 95%, and most preferably at least about 97%.

Embodiments described herein advantageously provide yields of soluble protein of at least about 50%, preferably at least about 60%, and more preferably at least about 70% based on the weight of protein in the raw material. The yield can be measured in various ways, such as by using the Kjeldahl method, which is well known in the art, and determines the amount of protein by weight by measuring the amount of nitrogen present in a sample. Typically in the Kjeldahl method, the total protein by weight of the raw material (using a representative sample) is measured and compared to the total protein by weight of the soluble protein end product (using a representative sample).

An example of yield calculation is as follows: 1000 kg of raw material is hydrolysed. This raw material contains 20% protein in wet weight (analyzed sample), giving a total of 200 kg protein into the system. This amount gives 300 kg of hydrolysate with 50% dry matter (weighed after evaporation) with a protein concentration of 88%. This means that this fraction contains 132 kg protein, which translates to a yield of 66% (150 kg dry matter with 88% protein=132 kg protein, which is 66% of the 200 kg protein put into the system).

The hydrolysate obtained from the processes and apparatuses described herein may refer to the aqueous component following separation, containing soluble proteins, peptides and amino acids. The term "hydrolysate" also may refer to various concentrated solutions of the aqueous component or even to the dry hydrolyzed protein matter, which can be obtained from the aqueous component by removal of water. The hydrolysate will constitute some percentage of the aqueous component as it comes from a separator, e.g., which takes out the fine solids.

In embodiments of this invention, for example, the aqueous component, which may itself be referred to as a hydrolysate, comprises soluble protein from about 0.1% to about 20%, preferably from about 1% to about 15%, more preferably from about 2% to about 12% and even more preferably from about 4% to about 10% and most preferably from about 6% to about 8% D.M. (dry matter) (that is, as measured by dry protein weight based on the total weight of the aqueous hydrolysate compared to the total weight of soluble protein contained therein after the hydrolysate has been evaporated).

In an embodiment, the hydrolysate at this time is evaporated so it contains approximately 50% D.M. and then an acid such as formic acid is added to provide resistance to microbes and the hysrolysate which may then be sold as animal feed or as similar products. However, this percentage can be greater or less depending on the desired dry matter content. For example, the hydrolysate can be dried further to a powder (more than 90% D.M.) and in this embodiment an acid need not be added to provide resistance to microbes.

J. ENZYMES

Many different types of enzymes can be used to hydrolyze the raw material. The type of enzyme or mixture of enzymes used will depend on the raw material that is being hydrolyzed. For example, proteolytic enzymes and endopeptidase and exopeptides mixtures may be used with protein-containing raw materials, such as fish, poultry, and beef, lamb, and other meats. Proteolytic enzymes (or "proteases") include Alcalase®, Neutrase®, Protamex®, and mixtures thereof, each of which can be obtained from Novozymes of Denmark. Endopeptidase and exopeptidase mixtures include Flavourzyme® (Novozymes of Denmark). Other proteolytic enzymes that can be used include Pescalase®, made by Gistbrocades of the Netherlands, and Promo 31® made by Biocatalysts Ltd. of Wales. Combinations also can be employed, for example, about 300 grams of Alcalase® and about 900 grams of Neutrase® per ton raw material can provide acceptable results for farmed Atlantic salmon. Moreover, proteases present in the raw material, for example, fish proteases contained in the raw material itself may be used. Also naturally occurring proteases isolated from mammalian or other species can used.

When raw materials of vegetable origin are used, it may be necessary to add carbohydrate-splitting enzymes, i.e., carbohydrases, to break down the carbohydrates in the material as well, various cellulose-, carbohydrase- and gluconase-based enzymes or enzyme combinations, such as Cellulase 13L (Biocatalysts), can for this embodiment.

The enzyme amounts employed depends on the type and composition of the raw material, as well as the operating parameters (e.g., temperature and rate of hydrolysis) set by the operator. The main guideline is that the amount of enzyme used sufficient to produce the type and amount of desired product. In theory, the amount of enzyme used may be determined based on the activity of the enzyme and the number of peptide bonds that are required to be broken, but the practicalities of the operations, including time and temperature, will require some routine experimentation to determine the point where hydrolysis no longer increases even with increasing enzyme addition, for a specific enzyme or combination. Taste of the resulting product also can vary depending on the enzyme used and may be factored into the decision of what enzyme(s) to use. Typically, information regarding the optimal amount of enzyme that may be used to hydrolize a given amount of raw material, for a given enzyme, is provided by the manufacturer of the enzyme.

Most enzymes are not active environments above 85° C. or below about 20° C. Thus, the temperature range in the hydrolysis area advantageously is maintained between about 20° C. and about 85° C., more preferably between about 50° C. and about 60° C., and most preferably at about 55° C.

K. THE FIGURES

FIG. 1 illustrates an embodiment of a hydrolysis apparatus (or system or plant) in greater detail. A collection area 10 comprises a raw material container 12 and a raw material disintegrator 14. The disintegrator may, for instance, be a meat mincer or a blender, in which the raw material is finely divided and reduced into smaller-sized pieces, typically between about 15 mm to about 50 mm. In one embodiment, the raw material size is reduced in a controlled manner to provide raw smaller raw material pieces that is sufficient to substantially avoids or minimize emulsification. The raw material is then conveyed to one or more hydrolyzers in the hydrolysis area 20, particularly to a tank 22 where the raw material is admixed and contacted with partly warm water (e.g., at a temperature between about 20° C. to about 85° C.) and a continuously supplied suitable proteolytic enzyme.

Alternatively, the warm water can be added to the raw material prior to being conveyed to the tank 22. One advantage of adding the warm water before the raw material reaches the tank 22 is that, especially during winter or with raw material preserved in a cold or frozen environment, the raw material can be cold and the water added can be hot, preferably close to 100° C., so that the mixture of cold raw material and hot water achieves an equilibrium temperature of approximately 50° C. to 60° C., which is the optimal temperature range for effective enzyme action. If the water is added to the raw material in the tank 22, in the collection area 10, or even mixed with the raw material before it is introduced into the collection area 1, the mixture of cold raw material and hot water will have ample time to achieve the desired equilibrium temperature of approximately 50° C. to 60° C., before the enzyme is added. The enzyme can be added any time after the desired temperature is achieved, either in the collection area 10, and/or in the hydrolysis area 20. Thus, the average temperature in the collection area advantageously will range between 5° C. (temperature of cold raw material) and 60° C. (temperature of cold raw material and water after reaching equilibrium).

In the embodiment of FIG. 1, the reaction mixture of disintegrated raw material, enzyme and water is fed into a hydrolysis reactor 24 and, by means of a first feeder screw (not shown) of the same diameter as the hydrolysis reactor 24, passes through it at a feeder rate so determined as to allow the enzymes to have hydrolyzed the greater part of the raw material when it has reached the exit from the hydrolysis reactor 24. The reaction mixture is kept at the optimal hydrolysis temperature appropriate for the enzyme, so that the meat portion is dissolved, leaving the cleansed bones at the bottom of the hydrolysis reactor 24.

The feeder rate is determined by taking into account the dimensions of the hydrolysis reactor 24 and the supply rate of the reaction mixture, as well as the exit rate of the reaction mixture from the hydrolysis reactor 24 into an inactivation area 30. The feed rate can be controlled by a person or by a computer that monitors the various parameters of the hydrolysis area and modifies the feed rate to achieve desired results.

The inactivation area 30 comprises an inactivation reactor 32, with an entry end 33 having an inlet and an exit end 34 having one or more outlets 34 and 36. The inactivation reactor can be any shape or size and preferably is a tube reactor surrounded by a heating mantle 37. The cross section shape of the inactivation reactor can also be, for example, U-shaped, V-shaped or triangular, a parallelogram (e.g., square, rectangular, diamond-shaped etc,), oval and the like. Admixing of reaction mixture with the heat released from the heating mantle 37, in order to denature the enzyme present in the reaction mixture, as well as other ingredients of protein origin, takes place by means of a rotating second feeder screw (not shown) of a diameter smaller than the inactivation reactor 32 and positioned at a distance from the bottom of the inactivation reactor 32. The second feeder screw serves, partly by means of its rotation, to conduct heat from the heating mantle down into the reaction mixture, and partly to shift the mixture onward towards the exit end 34 of the inactivation reactor 32. The feeder screws, as well as the rate of egress of the various components, can be controlled by a person or by a computer that monitors the various parameters of the inactivation area and modifies the different parameters, such as residence time and heat, to achieve desired results.

At the exit end 34 of the inactivation reactor, substantially all enzymatic activity has stopped, at which point protein and peptides have been denatured by heat and may exist either as water-soluble or water-insoluble ingredients of protein origin. The originally fed raw material has, at this stage of the method, been substantially transformed into a solid component 38 and a liquid component 39. The solid component 38, primarily comprising the cleansed bones and/or scales, is discharged through the outlet 35 in the exit end 34 of the inactivation reactor 32 and, after drying, can be processed into bone meal or fertilizer.

The liquid component 39, comprising fat and the aforementioned components of protein origin, is let out through the outlet 36 in the exit end 34. In some embodiments, it may be preferable to homogenize or mix the liquid layer 39, while in other cases, mixing or homogenization will not be beneficial. Advantageously, any such mixing or homogenization will not result in additional emulsification. In either case, the liquid component 39 is conveyed to a final processing or separation area 40. In FIG. 1, the final separation area 40 comprises a decanter or tricanter 42 that may be used to fractionate the liquid component into a fat fraction 44, a fraction comprising water-soluble ingredients of protein origin 46, and a fraction comprising water-insoluble ingredients of protein origin 48.

The composition of the continuously fed raw material may vary considerably, and the size and the extent of the individual phases and fractions may therefore also vary considerably. Consequently, in some situations and for some raw materials it may be difficult to arrange separate outlets for the fractions of the liquid layer sufficiently precisely. Although it may not always be a problem, there can be with some raw materials a risk that, for instance, the fat component and the aqueous component contaminate each other and even clog their respective outlets. This can make it difficult to discharge the pure separated product phases and fractions continuously from the exit end 34 of the inactivation reactor 32.

Also, it may be undesirable to have the continuously rotating first and second feeder screws to continue to push material towards potentially clogged outlets. There can be a risk, in these instances, of the inactivation reactor 32 filling to a capacity that prevents the feeder screws from functioning optimally. The pressure forces upon the reactor walls and upon joints in the pipelines can increase enormously with the ensuing risk of leaks or explosions. To prevent this, the plant can be stopped and cleaned occasionally.

Figure 3:
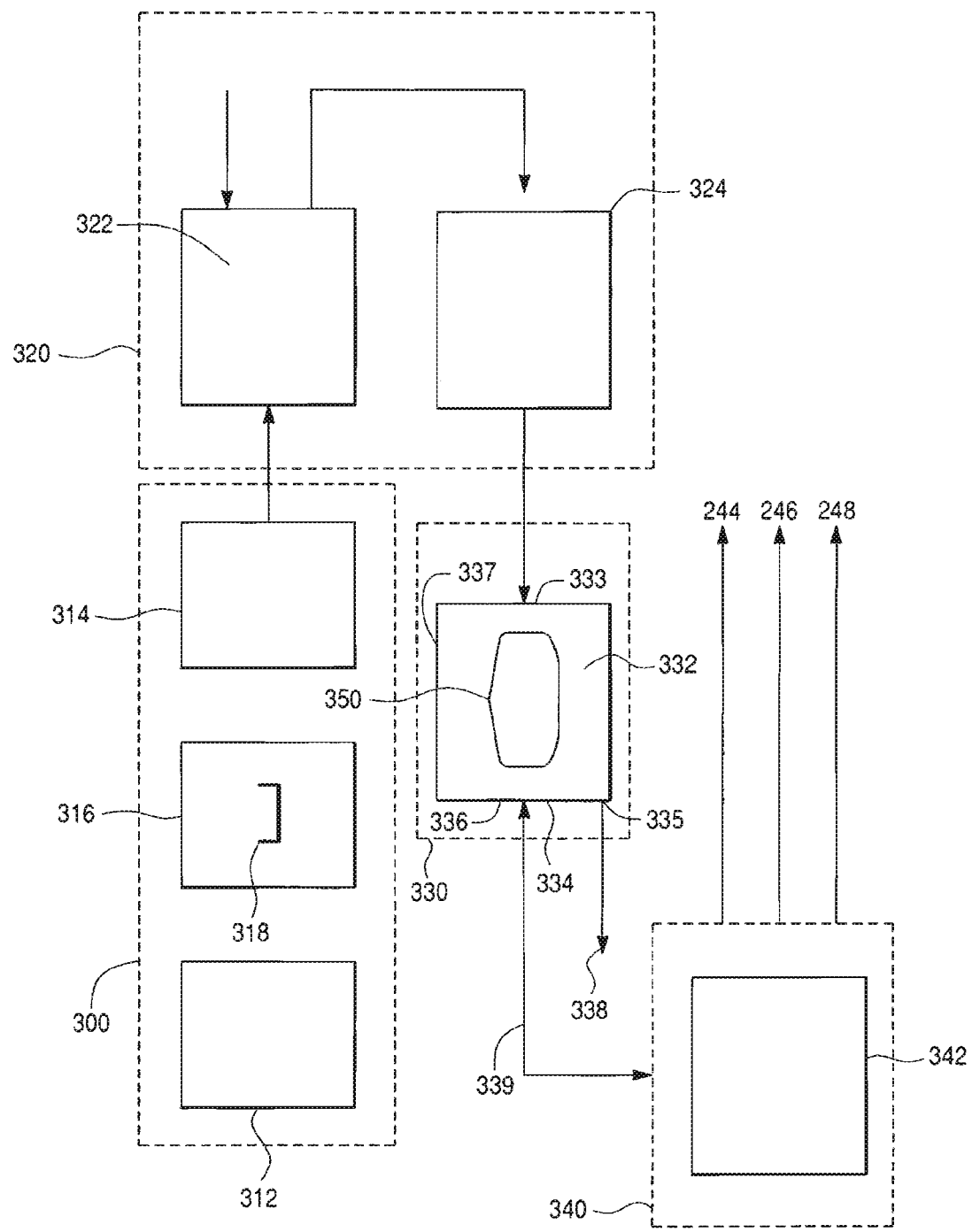
FIG. 3 is a block diagram of another embodiment that includes a reactor that keeps the liquid phase in circulation.

In those cases where homogenization is preferred, the liquid component can optionally be homogenized with a blender impeller 50, an agitator, a circulation pump, which keeps the suspension circulated and substantially uniform or homogenous, as shown in the inactivation reactor 332 in FIG. 3, or the like. The blender impeller 50, for example, can be positioned in the inactivation reactor 32 in connection with the outlet 36 for the homogenized liquid component. Hereinafter the term "homogenized liquid component" will be applied in describing the liquid component's homogenous suspension of fat and aqueous components. The blender impeller 50 is only required if homogenization is preferred, and if homogenization is not preferred, then the inactivation reactor 32 can be provided without a blender impeller 50 or the blender impeller 50 can simply be turned off. The blender impeller 50 homogenizes the liquid component and suspended ingredients in order to form a homogenized liquid component, so that this homogenized liquid component or parts of it does not accumulate in front of and block the outlet 36. With homogenization, adapted to the type and composition of the raw material, the heat-treated liquid and/or suspended reaction mixture is discharged continuously and without interruption through the outlet 36 in the exit end 34 of the inactivation reactor 32. Thus, optionally a liquid component rich in fat can be admixed during vigorous homogenization.

As discussed above, dissolved and non-dissolved ingredients in the form of proteins, amino acids and peptides, resulting from or remaining after the hydrolysis area 20, and the subsequent denaturing and inactivation of these by means of suitable agents produced in the inactivation area 30, may be mixed to form a substantially homogenous suspension, which may readily and speedily be let out continuously and separated from the solid matter component 38. This embodiment makes no requirements as to the composition of the raw material and is less sensitive to the positioning of the outlets from the inactivation reactor 32.

The homogenized liquid component is next conveyed to a separation area 50. The separation assembly includes a continuously functioning decanter or tricanter 42 for final separation.

In the instance where a decanter is used, the homogenized liquid component is fractioned into a fat fraction and an aqueous fraction with soluble and insoluble ingredients.

In the instance where a tricanter is used, the aforementioned homogenized liquid component is fractioned into a fat fraction 44, an aqueous fraction with water-soluble ingredients 46, and a fraction with water-insoluble ingredients 48, preferably in the form of denatured proteins and peptides which are generally non-dissolvable or heavily non-dissolvable in water, as a result of their hydrophobic side chains exposed in the denaturing.

The end fractions obtained further may be purified or used directly as a nutrition supplement. Furthermore, the soluble protein fraction has been found to be a valuable source of proteins, peptides and amino acids for use in industrial fermentation, fertilizers, animal feeds, culture medium, and nutritional and food supplements. It has been found that the hydrolysate extracted from the protein soluble fraction has a biological digestibility coefficient of 90% or above, and more specifically 95-97%.

Thus, it is possible to utilize many different types of waste products from the food industry, which would otherwise have to be incinerated to be eliminated. Accordingly, such waste products may now become a valuable resource in the food industry.

For instance, essential fatty acids and oils, such as omega-3 fatty acids, may be extracted from the fat fraction 44. A solid component 38 in the form of cleansed bones may be used in the production of bone meal for use in animal feed. Fractions in which the content of dry matter stems from proteins, may be used in enriching foods by proteins, peptides or amino acids. A fraction without bitter hydrophobic amino acids will in particular be preferred for foods for humans. Alternatively, the protein fraction may be used for animal feed.

In yet another embodiment, in which a low fat content in the end product is desired, the fat component or part of the fat component can be withdrawn or removed from the inactivation reactor 8 batch wise or continuously from the top of the inactivation reactor 8 separately from the aqueous component. The remaining aqueous component may contain small amounts of fat droplets, but for the most part will comprise water-soluble and water-insoluble ingredients. In the case of some raw materials, the resulting reaction mixture can be discharged as independent fractions through independent outlets in the exit end of the inactivation reactor 32. Otherwise, the fractions can be separated in the separation area 40.

Figure 2:
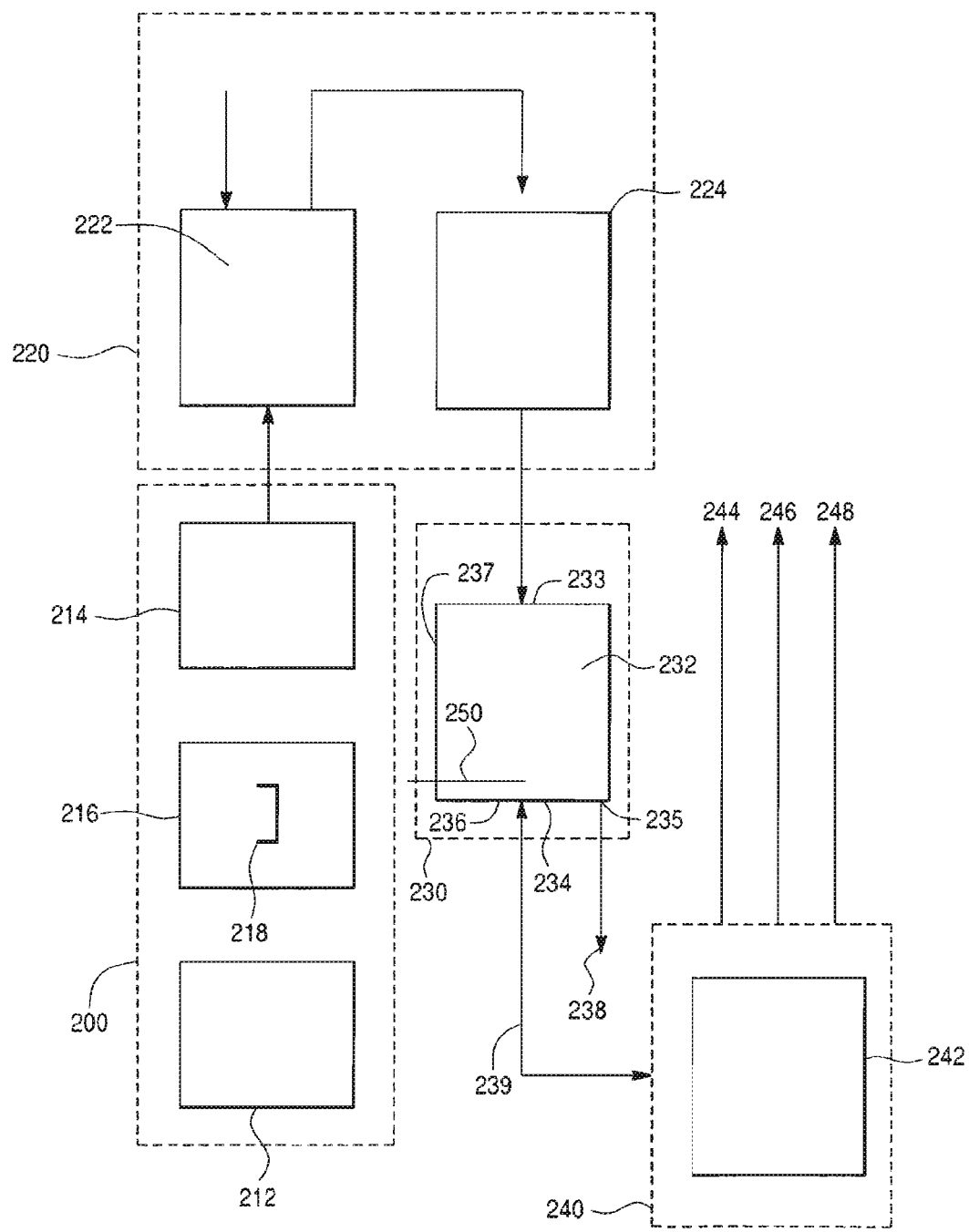
FIG. 2 is a block diagram according to another embodiment of an apparatus for removing metal parts from raw material.

FIG. 2 shows an additional embodiment for the hydrolysis described with respect to FIG. 1. In this embodiment a preparation section 200 has a further section 216 interposed between a raw material container 212 and a disintegrator 214, for the purpose of removing metal containing ingredients, such as fishing hooks, shots and broken knife edges, from the raw material. In the example shown, the section 216 has a magnet 218.

A hydrolysis section 220 receives raw material from the preparation section 200 and hydrolyzes it. The hydrolysis section includes a tank 222 where the raw material is mixed with warm water and enzyme. A hydrolysis reactor 224 receives the mixture of raw material, enzyme and water from the tank 222 and conveys it onward to an inactivation section 230.

The inactivation section includes an inactivation reactor 232 that receives the hydrolyzed or partly hydrolyzed reaction mixture through an inlet located at the entry end 233. The inactivation reactor includes a heating mantle 237 and outlets 235 and 236 in its exit end 234. The enzyme in the reaction mixture is inactivated in the inactivation reactor 232 and a solid component 238 of the reaction mixture is discharged through a first outlet 235, while a liquid component 239 is discharged from a second outlet 236 separate from the first outlet 235 and positioned at a distance from the first outlet 235. A blender impeller 250 operating within the inactivation reactor 232 can also be included to homogenize the reaction mixture.

A separation area or section 240 receives the liquid component 239 into a decanter tricanter, which centrifuges it into three fractions: a fat fraction 244; a liquid fraction comprising water soluble ingredients of protein origin 246; and a fraction comprising water-insoluble ingredients of protein origin 248.

FIG. 3 shows an additional embodiment for hydrolysis. In this embodiment, the inactivation reactor 332 has no blender impeller. Instead the liquid phase is kept in circulation in the inactivation reactor. The circulation may for instance be maintained by a circulation pump, which is not shown.

As before, a collection area 300 has a raw material container 312, a raw material disintegrator 314, and a further section 316 interposed between the raw material container 312 and disintegrator 314, for the purpose of removing metal containing ingredients, such as fishing hooks, shots and broken knife edges, from the raw material. In the example shown, the section 316 has a magnet 318.

A hydrolysis section 320 receives raw material from the preparation section 300 and hydrolyzes it. The hydrolysis section includes a tank 322 where the raw material is mixed with warm water and enzyme. A hydrolysis reactor 324 receives the mixture of raw material, enzyme and water from the tank 322 and conveys it onward to an inactivation section 330.

The inactivation section includes an inactivation reactor 332 that receives the hydrolyzed or partly hydrolyzed reaction mixture through an inlet in its entry end 333. The inactivation reactor includes a heating mantle 337 and outlets 335 and 336 in its exit end 334. The enzyme in the reaction mixture is inactivated in the inactivation reactor 332 and a solid component 338 of the reaction mixture is discharged through a first outlet 335, while a liquid component 339 is discharged from a second outlet 336 separate from the first outlet 335 and positioned at a distance from the first outlet 335.

A separation area or section 340 receives the liquid component 339 into a decanter or tricanter 342, which centrifuges it into three fractions: a fat fraction 344; a liquid fraction comprising water soluble ingredients of protein origin 346; and a fraction comprising water-insoluble ingredients of protein origin 348.

With respect to any one of the embodiments described herein, the reaction mixture is kept at the optimal hydrolysis temperature appropriate for the enzyme, so that the meat portion is dissolved, leaving the cleansed bones at the bottom of the hydrolysis reactor. The feeder rate is determined by taking into account various parameters such as the temperature and particular enzymes used, the dimensions of the hydrolysis reactor and the supply rate of the reaction mixture, as well as the exit rate of the reaction mixture from the hydrolysis reactor.

Figure 4:
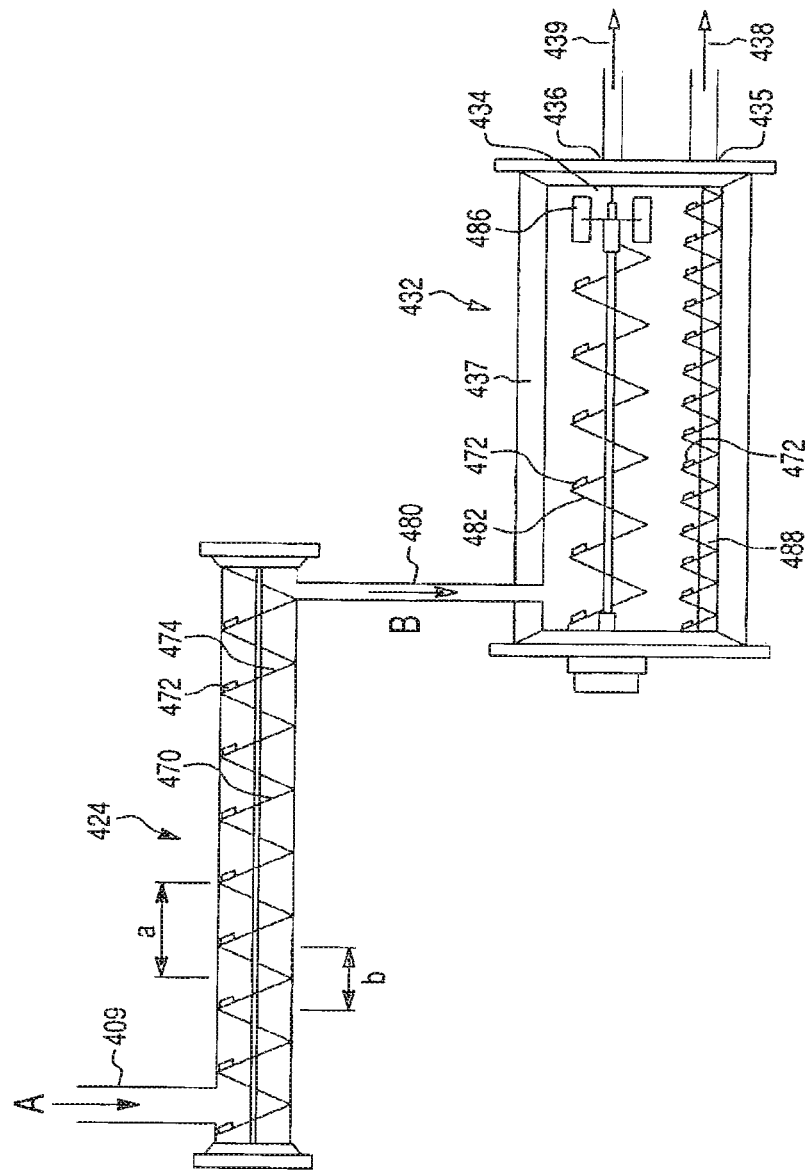
FIG. 4 is a side elevation view of a hydrolysis reactor and an inactivation reactor according to one embodiment.

FIG. 4 shows a schematic cross section of a hydrolysis reactor 424 according to an embodiment of the invention. A reaction mixture (e.g., having a temperature of between about 20° C. and 85° C. and preferable 50° C.-60° C. and more preferable about 50° C.) of raw material, such as comminuted fish parts, enzyme and water, is added through the inlet end 409 of the hydrolysis reactor 424 as shown by the arrow A. The hydrolysis reactor 424 can be designed with a first feeder screw 470 with threads 474 of approximately the same diameter as the inner diameter of the hydrolysis reactor 424. Each thread 470 can include a scoop 472 located at the periphery of the screw for mixing and carrying the reaction mixture towards the exit 480 of the hydrolysis reactor 424. In a first period of time, the first feeder screw 4700 shifts the reaction mixture a distance "a" in the direction of the exit 480. In a subsequent second period of time, the rotation direction of the first feeder screw 470 is reversed, thereby pulling the reaction mixture a distance "b" which is shorter than the distance "a", back towards the inlet end 409 of the hydrolysis reactor 424. The reversing movement provides optimal hydrolysis conditions and shifts the increasingly hydrolyzed reaction mixture continuously onward towards the exit 480 and over into the inactivation reactor 432, as shown by the arrow B. The hydrolysis reactor 424 can be horizontally oriented as shown, vertical or at an angle from between about 1° to 89° (not shown). If vertically oriented, the input end can be above the output end, such that the reaction mixture is assisted toward the output end by gravity. Alternatively, the output end can be above the input end, such that the reaction mixture is advanced toward the output end against gravity.

The inactivation reactor 432 is arranged with second and third feeder screws 482 and 488, both of which may, in a manner similar to the first feeder screw 470, optionally be designed with scoops or sheets 472 for carrying the reaction mixture. The second feeder screw 482 typically makes the same reversing movement in the inactivation reactor 432 as does the first feeder screw 470 in the hydrolysis reactor 424. The diameter of the second feeder screw 482 is smaller than the diameter of the inactivation reactor 432, to allow for room so that the third feeder screw 488 can shift a solid matter component in the form of cleansed bones and other solid ingredients out through the outlet 435 in the exit end 434 of the inactivation reactor 432. The inactivation reactor is surrounded by a heating mantle 437, maintaining a temperature suitable to inactivate the hydrolysis enzyme, for example, of between about 85° C. and about 100° C., preferably about 95° C. It has been found that separation of the different components is best achieved when the reaction mixture is maintained within this temperature range and preferably at about 95° C.

By combining and adapting the operational parameters, such as the temperature, length of the reactors 424, 432 and the amount of raw material in it, to the type, the quantity and the concentration or the enzyme in combination with the rate of the feeder screws 470, 482, 488 and the number and the length "a" and "b" of the movements of the feeder screws, it is possible to optimize the holding time in the reactors 424, 432 and thus the reaction and inactivation time. The optimal operation parameters by means of which it is possible to control the proportion of amino acids which lend a bitter flavor to the hydrolysate, and keep it as low as possible, can be determined empirically or by theoretical determination, optionally followed by control measuring.

An outlet for a phase or fraction is, as mentioned above, arranged in the exit end of the inactivation reactor 432, emerging from a plane which is parallel to and intersecting a plane in the inactivation reactor 432 where the phase or fraction adjusts itself. An outlet extends across a part of the thickness of that phase or fraction, thereby ensuring rapid continuous outlet of phases and fractions without them contaminating each other.

Variations of the foregoing apparatus and method can be envisaged. For example, a fat component may be collected and utilized independently or re-admixed with the aqueous component, before the mixture is post-processed in the final treatment section.

Alternatively, the second feeder screw 482 may be given a diameter so large (not shown) that it may be used simultaneously for carrying the solid phase onward towards the outlet 435. In another embodiment (not shown), the second feeder screw 482 can be given a diameter, which fills the entire inactivation reactor 432, and a length, which allows space for a comparatively short third feeder screw 488.

In FIG. 4, the third feeder screw 488 is shown as being positioned in its entirety along the bottom. It may, however, be appropriate to let at least part of the third feeder screw 488 rise above the liquid component in order to sift it off before the solid matter component is let out from the inactivation reactor 432. In such an embodiment (not shown) the outlet for the solid matter component would be situated above the outlet for the liquid component.

Figure 5:
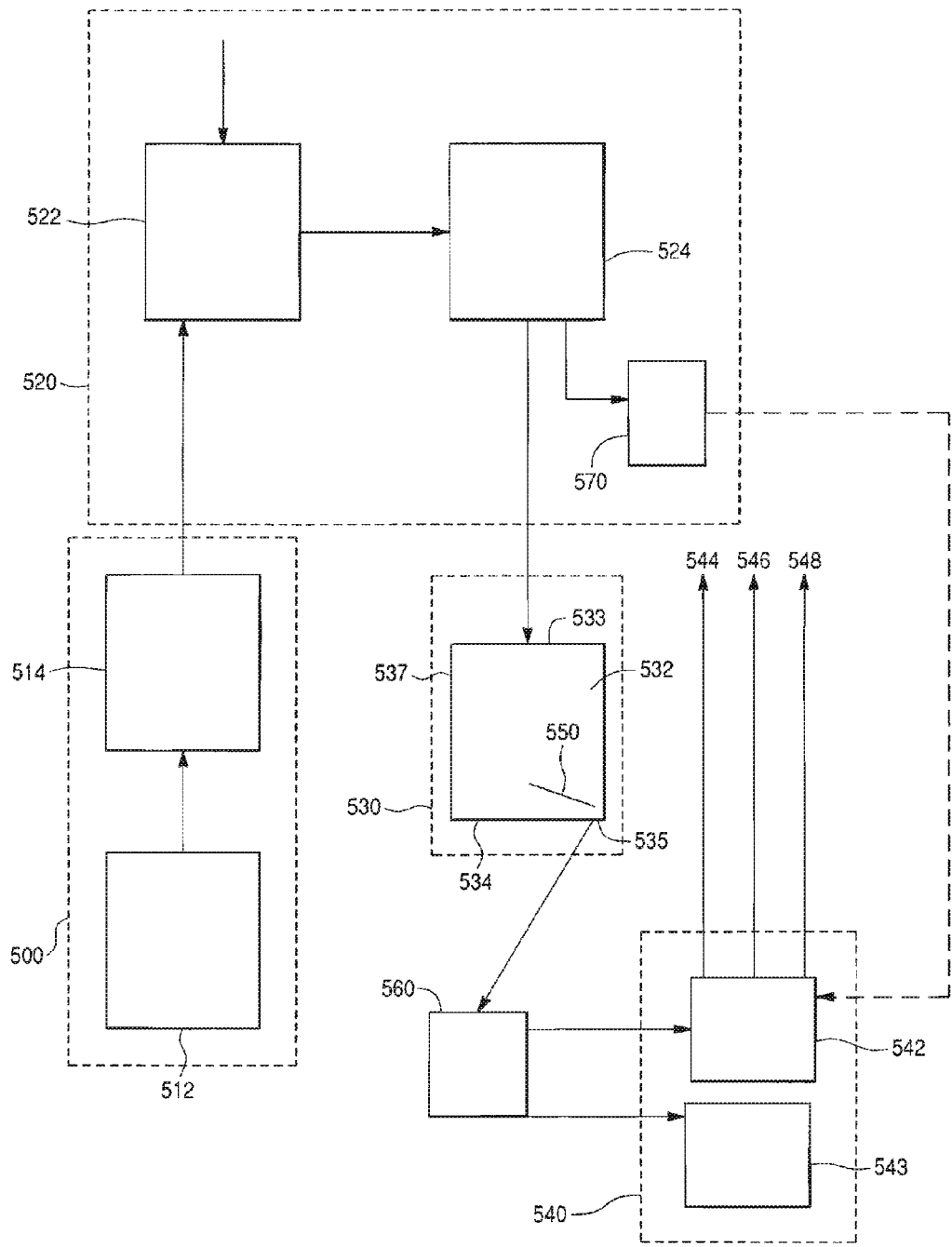
FIG. 5 is a block diagram of another embodiment that includes removal of oil from the hydrolysis assembly.

Turning to FIG. 5, a system is depicted for controlling the level of emulsification in the reaction mixture. A preparation area 500 has a raw material container 512 and a raw material disintegrator 514. The disintegrator 514 may for instance be a meat mincer or a blender by means of which the raw material is finely divided into smaller ingredients in a gentle manner that substantially avoids emulsification. The raw material is then carried onwards to a hydrolyser in the hydrolysis area 520. In the hydrolysis area 520 the finely divided raw material is conveyed onwards to a tank 522 where it is admixed with partly warm water and a continuously supplied suitable proteolytic enzyme. The reaction mixture of disintegrated raw material, enzyme, and water is fed into a hydrolysis reactor 524 and, by means of a first feeder screw (not shown) of, for example, approximately the same diameter as the hydrolysis reactor 524, passes through it at a feeder rate so determined as to allow the enzymes to have hydrolyzed the greater part of the raw material when it has reached the exit from the hydrolysis reactor 524. The feeder screw rate should also be set so as to minimize emulsification, with separate fat and aqueous components forming with limited emulsion. The aqueous component may have fat droplets dispersed through it, but emulsification can be controlled. Only 5%, and preferably only 2%, and preferably less than 2%, and very preferably less than 1%, and most preferably less than or equal to about 0.5% of the reaction mixture is emulsified. The feeder screw can operate with low sheer forces with a substantially slow rotation to control emulsification. In this manner, the reaction mixture is conveyed slowly, such that emulsification is controlled.

If the percentage of emulsification is above a desirable amount, such as 0.5%, then the hydrolysis reaction can be modified to reduce the percentage of emulsification to acceptable levels. Emulsification can be controlled in various ways, such as chemically (chemical emulsion control and/or demulsification) or physically (physical emulsion control and/or demulsification).

In one embodiment (not shown), an optional pump can draw a portion of the fat component formed in the reaction mixture away from the hydrolysis reactor 524 and deposit the fat in a fat holding container 570. The fat from the fat holding container 570 can then be processed into various end products. This modified embodiment also improves the quality of the recovered fat, because the fat is not exposed to the high heat levels found in the inactivation area 530. Alternatively, or additionally, fat can be removed from the inactivation area.

Alternatively, as shown in FIG. 5, the fat from the fat holding container 570 can be transferred to the separation area 540 or directly to the decanter or tricanter 542, for further processing in conjunction with the aqueous component.

Meanwhile, the remainder of the reaction mixture contains mostly a solid matter component and an aqueous component, with the aqueous component advantageously having low or substantially no emulsion. The reaction mixture is conveyed from the hydrolysis reactor 524 to the inactivation area 530 using either a single conveyor screw configuration or a double conveyor screw configuration as described above with respect to FIG. 4. In the inactivation area 530, the reaction mixture enters the inactivation reactor 532 where the enzymes in the reaction mixture are inactivated as explained above. The inactivation reactor 532 includes only one outlet 535 for both the aqueous component and the solid matter component, which will be discharged from the outlet together. The inactivation reactor 532 can also include a mild agitator 550 that rotates in the reverse direction to prevent solid matter from clogging the outlet 535. The mild agitator 550 lifts solid matter blocking the outlet 535 into the reaction mixture and it is discharged in combination with the aqueous component. A pump can be used to draw out the reaction mixture and pump it to a filter screen 560 where it is deposited. The filter screen 560 filters away the solid matter component and deposits it in a solid matter container 543 associated with the separation area 540. The aqueous component is deposited in the decanter or tricanter 542 associated with the separation area 540.

Figure 6:
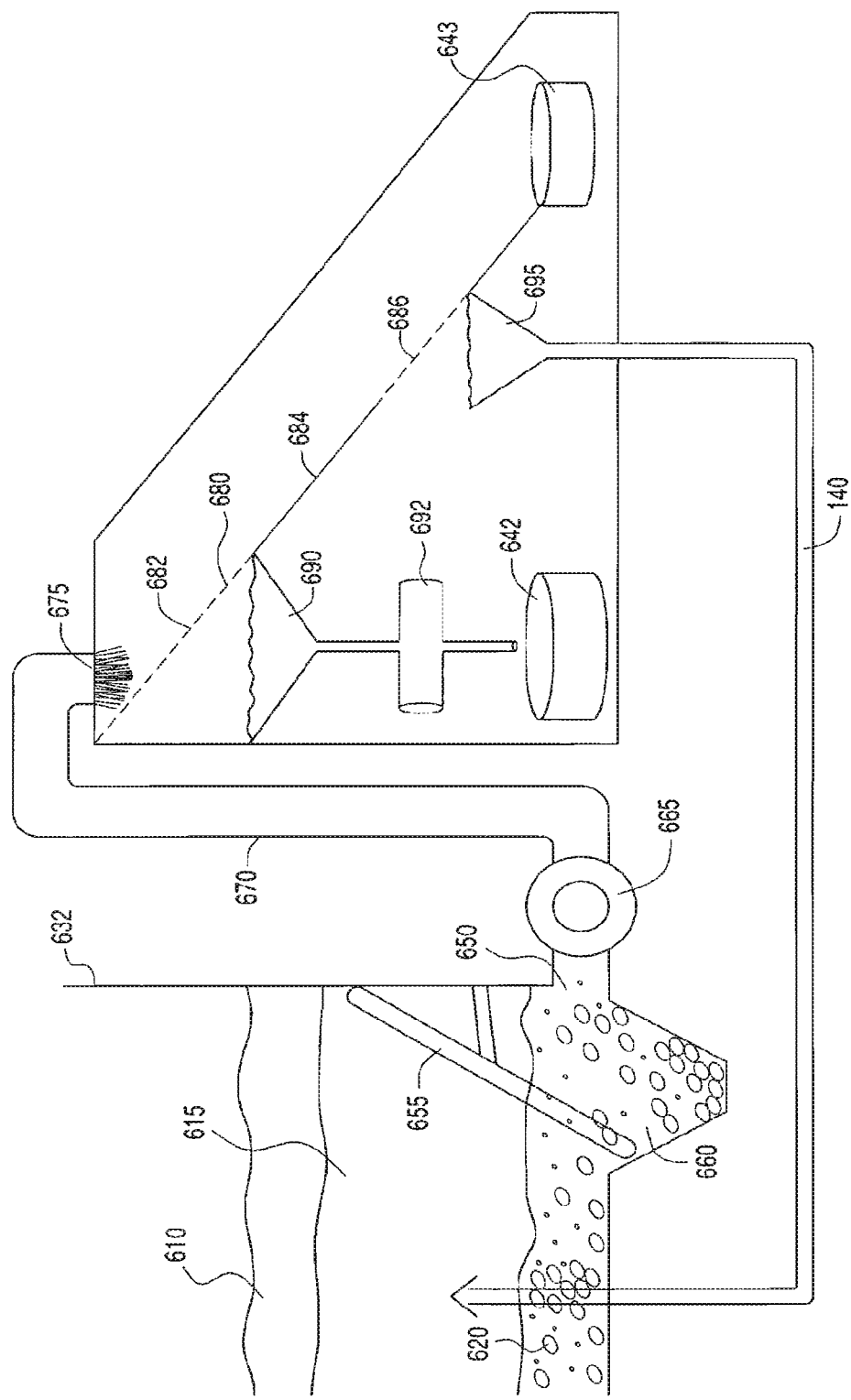
FIG. 6 is a diagram showing an inactivation reactor, a slanted filter screen and separate solid and liquid collection containers for use in an apparatus and process for hydrolyzing animal or vegetable raw material.

FIG. 6 illustrates a filtration system which may be used as described herein. The reaction mixture includes a fat component 610, an aqueous component 615 and a solid matter component 620 all advancing toward the outlet 650. As described above, in certain circumstances much of the fat component 610 can be removed from the hydrolysis reactor, but in other circumstances the fat component 610 will remain, and the aqueous component 615 will also contain some fat droplets unless the raw material is substantially fat free. In any case, the solid matter 620 is agitated by a mild agitator 655 that rotates in a reverse direction with respect to the outlet 650. This reverse rotation lifts the solid matter sediment forming near the outlet 650 so that the outlet 650 is not blocked by the sediment. A trough 660 adjacent the outlet 650 also controls the amount of outlet 650 blockage, because any sediment not churned by the mild agitator 655 rests at the bottom of this trough 660 and away from the outlet 650. A large, high capacity pump 665 operating at low speeds pumps the reaction mixture up through pipe 670. A low speed, high capacity pump 665 will cause less emulsification than a high speed pump.

The reaction mixture is pumped toward a nozzle 675 from which the reaction mixture is discharged onto a filter screen 680. The filter screen 680 is slanted downward and includes a first filtration region 682, followed by a nonporous region 684, which is followed by a second filtration region 686. The first and second filtration regions 682 and 686 are permeable to the fat and liquid forming the fat component 610 and the aqueous component 615 but impermeable to the solid matter forming the solid matter component 620. The nonporous region 684 is impermeable to fat, liquid and solid matter. Beneath the first filtration region 682 is a funnel 690 that catches the fat and liquid filtering through the first filtration region 682. The fat and liquid tend to cool once they have been discharged from the inactivation reactor 632. Therefore, the fat and liquid caught by the funnel is lead to a heat exchanger 692, which heats the mixture back to between about 90° C. and about 110° C., more preferably between about 93° C. and about 97° C., and most preferably about 95° C. Thus, when the fat and liquid reach the tricanter, the temperature of the mixture in the tricanter should be between about 90° C. and about 110° C., advantageously between about 93° C. and about 97° C., and most advantageously about 95° C. It has been found that this increased level of heat tends to optimize separation of the fat and aqueous components in the tricanter 642, where it is centrifuged into three fractions: a fat fraction; an aqueous fraction containing water-soluble protein; and sediment containing insoluble protein.

Figure 9:
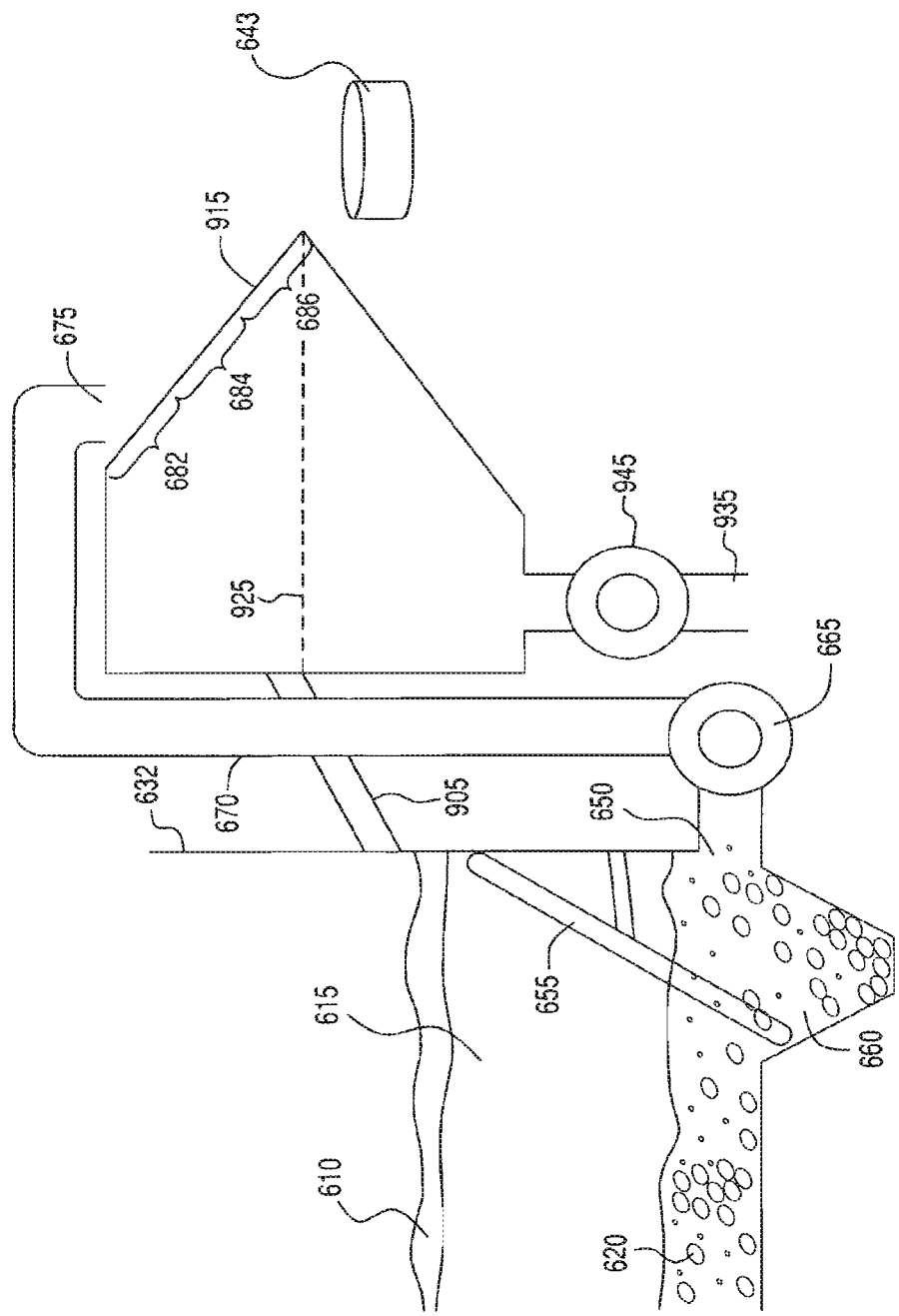
FIG. 9 is a diagram showing a variation of the filtration system of FIG. 6.

A second funnel 695 beneath the second filtration region 686 catches any remaining fat and liquid and a pump (not shown) pumps it back to either the inactivation reactor 632 for further processing, or back to the hydrolysis reactor (not shown) for further processing. Alternatively, the liquid and fat caught by the second funnel 695 can be pumped to the heat exchanger 692 and deposited into the tricanter 642 (via path 140). Additionally, an overflow return (with or without a pump) may be provided to return overflow reaction mixture to the inactivation reactor 632 or hydrolysis reactor in a similar manner as shown in FIG. 9. Meanwhile, the solid matter rolls down along the filtration screen 680 and into a solid matter container 643 for further processing. The solid matter is largely composed of bones, fish scales, rocks, dirt, sediment, and the like. The filtration screen 680 is capable of separating some of the solid matter from the liquid and fat, and preferably substantially all of the solid matter from the liquid and fat.

In the tricanter 642, the mixture of fat and liquid is centrifuged to obtain three separate fractions: a fat fraction; an aqueous fraction containing water soluble protein; and a sediment containing water insoluble protein. A suitable tricanter is made by Westfalia Surge of Germany model number CA 501-63-32. The number of suitable rpms and the suitable amount of material to pass through the tricanter per amount of time is provided by the manufacturer of the tricanter. For example, 4000 rpms and a differential speed of 4.3 can be used. The three fractions can be placed into separate areas and further processed.

In one embodiment, the aqueous fraction containing the water soluble protein is further purified by centrifuging in a second centrifuge or separator for example a GEA Westfalia Separator AG, model number MSD 90 (not shown). This removes any remaining fine particles of insoluble protein. At this stage, the aqueous fraction is still a clear solution with about 8% dry matter. Next, the aqueous fraction containing water-soluble protein can be dried using an evaporator (not shown) to evaporate water, reducing the solution to 50% dry matter. At this stage, the solution is a syrupy product to which acid can be added for preservation. The product can be further dried using additional drying equipment to reduce it to 90-95% dry matter.

According to one embodiment as shown in FIG. 9, filter screen 915 (similar to filter screen 680 of FIG. 6) is elevated from fluid level 925. By elevating filter screen 915 relative to fluid level 925, a pump-free overflow return 905 may be provided, the pump-free overflow return 905 being positioned approximately at a bottom portion of filter screen 915 as indicated by level 925. This configuration eliminates the need for a pump (e.g., a low speed, high capacity pump) to return overflow reaction mixture to the inactivation reactor 632 as shown or to the hydrolysis reactor. It should be appreciated, however, that a pump may be provided for pumping overflow reaction mixture via overflow return 905 for some applications.

As with the filter system shown in FIG. 6, a funnel 690 (not shown in FIG. 9) may be provided to catch the fat and liquid filtering through the first filtration region 682. The caught material may be pumped to a heat exchanger 692 using a low speed, high capacity pump 945 via pipe 935. Additional components, such as funnel 695 shown in FIG. 6, may also be provided, as would be readily apparent to one of ordinary skill in the art after reading this disclosure.

Thus, employing the apparatuses and methods taught herein, it is now possible to maintain an even and continuous outlet and flow to the decanter (even with a highly complex composition of the raw material) which gives a quantity and composition of heat treated hydrolysis products.

L. EXAMPLES

Example 1

By using a method and system similar to that illustrated in FIG. 1, a mixture of waste fish material in the form of bones and fish heads from cod is gently minced at a rate of 3 tons per hour through an orifice with holes of a diameter of 30 mm. The minced fish mixture is conveyed onward at the same rate to a blender vat where boiling water is added at the ratio 1:1. At the exit from the blender vat the temperature is measured as 55° C. To the hot fish mixture was added 1 g of Novo Alcalase® 2.4 per kg mixture, whereafter enzyme and fish mixture was carried onward to an 8 m long tube-shaped hydrolysis reactor, which had a diameter of 0.9 m. In the hydrolysis reactor the fish mixture with enzyme was slowly carried forward in the longitudinal direction of the tube towards the exit from the hydrolysis reactor by a feeder screw with threads, which have a pitch of 50%. Each thread was along its periphery equipped with sheets of a size of 200 mm×200 mm×300 mm. The passage of the hydrolysis reactor took 40 minutes, and the temperature of the mixture of fish waste and enzyme is measured at the exit of the hydrolysis reactor as 50° C.

The hydrolyzed mixture was conveyed onward to the inactivation reactor where the Alkalase® and the natural fish enzymes were inactivated, and proteins and peptides were denatured by heating by means of a surrounding steam mantle which maintained a constant temperature of about 120° C. The content of the inactivation reactor was forced onward towards the outlets in it by means of a feeder screw, with threads with a 50% pitch and scoops along the periphery of each thread. Halfway through the inactivation tank the temperature of the mixture was measured as 95° C. or higher. The liquid phase was homogenized with a powerful agitator until visible homogenizing was observed, and the solid phase in the form of cleansed bones was continuously removed from the bottom of the inactivation reactor by a feeder screw. The liquid phase comprised fat, oil, fatty acids, protein, peptides of varying length, amino acids, and water. The homogenized liquid phase is carried onward to a tricanter where it was split into three fractions, a fat fraction, an aqueous fraction with soluble parts, and an aqueous fraction with nondissolvable parts.

The centrifuging in the tricanter resulted in a 2 percent fatty fraction, 80 percent aqueous fraction with soluble in gradients from proteins, and 18 percent aqueous fraction with non-dissolvable ingredients proteins. Control readings of the composition of the aqueous fraction with soluble ingredients showed this to have a composition of 5 percent protein, 0.003 percent fat, and the remainder water. Control readings of the composition of the aqueous phase with non-soluble ingredients showed its composition to be 7 percent protein, 0.5 percent fat, and the remainder water.

The aqueous protein fractions obtained will have a pleasant flavor of cod and may be used as the basis for fish sauces and soups, or as an additive to products of fish meat. The bones from the solid phase may, following drying, be ground into bone meal. The fat fraction has a high content of saturated fatty acids and may be used in health food products.

Example 2

The method and apparatus used was similar to that of Example 1, but the raw material was the carcass from boned chickens. The agitation and the admixing in the hydrolysis reactor were furthered by firstly letting the feeder screw in the hydrolysis reactor rotate clockwise for a period allowing the chicken mixture with enzyme to be pulled back by 0.2 m in the longitudinal direction of the hydrolysis reactor. The fat fraction in the liquid phase was let out separately at the upper edge of the inactivation reactor, one meter before the agitator by means of a diaphragm pump. The fat fraction is pumped onward to the decanter where, before being added to it, is being admixed with the liquid phase from the inactivation tank.

The centrifuging in the tricanter resulted in 10 percent fatty fraction, 70 percent aqueous fraction with soluble ingredients from proteins, and 20 percent aqueous fraction with non-dissolvable ingredients proteins. Control measurings of the composition of the aqueous fraction with soluble ingredients showed its composition to be 6 percent protein, 0.004 percent fat and the remainder water. Control measurings of the aqueous fraction with non-dissolvable ingredients showed its composition to be 9 percent protein, 0.5 percent fat, and the remainder water.

The aqueous fraction with non-dissolvable ingredients from proteins may be used as a basis for soups or sauces or as an additive to meat products. The aqueous fraction with non-dissolvable ingredients from proteins may be admixed with meat products, such as minced meat, sausages and luncheon meat. The bones from the solid phase may be ground into bone meal after having first been dried.

The liquid phase is typically separated into a fatty fraction and one or more aqueous fractions. The non-dissolvable denatured aqueous protein fraction has a specific gravity different from the soluble denatured protein fraction, and these two fractions will therefore theoretically be separated from each other to such a degree that it is possible to let them out separately for additional post processing. This may be more difficult in practice, however, with some types of raw material.

Example 3

In this example, the raw material is salmon waste materials, such as filleted salmon including head. The end product, i.e., hydrolysate, is a white powder, which is substantially soluble in water at room temperature and which contains a mix of proteins, peptides and amino acids. At room temperature with moderate agitation there is no precipitation visibly observable to the naked eye. The starting material has 15-25% fat, with the remainder being protein and bones. The raw material is hydrolyzed substantially according to the method and system described with respect to FIG. 1, including controlled emulsification within the hydrolysis reactor and inactivation reactor as discussed with respect to FIG. 5. Emulsification is limited to two percent of the reaction mixture. Hydrolysis is carried out at a rate of approximately three tons per hour of raw material with an additional approximately three tons per hour of water. The process is carried out for seventy-two hours without stopping, thus processing approximately 216 tons of raw fish material and 216 tons of water. Continuous hydrolysis could have been carried out for a longer duration of time, up to thirty days, but the reaction is stopped at three days for cleaning of the reactors.

The reaction mixture after hydrolysis and inactivation of enzyme is deposited in a tricanter and centrifuged to form three fractions: a fat fraction; an aqueous fraction having water soluble protein at room temperature; and a sediment formed from insoluble protein. With respect to the water soluble protein, at room temperature with moderate agitation there is no precipitation visibly observable to the naked eye. The solute from the fraction containing water soluble protein is extracted and analyzed. A biochemical analysis of dry product provides the following data:

| CHEMICAL CHARACTERISTICS | |
|---|---|
| | Standard |
| Dry matter | 95 ± 2% |
| Protien (N × 6.25) | 88 ± 2% |
| Lipid (of DM) | 2 ± 1% |
| Ash | 5 ± 1% |
| Total amino acids | 81 ± 2% |
| Free amino acids | 12-14% |
| Peptides < 3000 Da | 60-63% |
| Chloride (as NaCl) | 1.5 ± 0.3% |

| MICROBIOLOGY | |
|---|---|
| | Standard |
| Total aerobic microbial count | <5000/g |
| *Salmonella* | Absence/25 g |
| Yeasts | <20/g |

| TYPICAL AMINO ACID DISTRIBUTION GIVEN AS g/100 g PROTEIN | | |
|---|---|---|
| Amino Acids | Abbr. | Total (T) |
| Alanine | Ala | 6.3 |
| Arginine | Arg | 5.6 |
| Aspartic Acid | Asp | 6.7 |
| Cysteine | Cys | 0.5 |
| Glutamic Acid | Glu | 11.1 |
| Glycine | Gly | 11.7 |
| Histidine | His | 2.8 |
| Isoleucine | Ileu | 2.3 |
| Leucine | Leu | 4.1 |
| Lysine | Lys | 5.2 |
| Methionine | Met | 2.0 |
| Phenylalanine | Phe | 2.1 |
| Proline | Pro | 6.0 |
| Serine | Ser | 3.8 |
| Threonine | Thr | 3.0 |
| Tryptophan | Trp | 0.5 |
| Tyrosine | Tyr | 1.5 |
| Valine | Val | 3.0 |
| OH-proline | OHpro | 3.1 |

| OTHERS | | |
|---|---|---|
| Taurine | Tau | 1.7 |

| MINERALS AND TRACE ELEMENTS | |
|---|---|
| Minerals | g/kg |
| Ca | 1.3 |
| K | 20.0 |
| Mg | 1.7 |
| Na | 22.0 |
| P | 10.3 |
| Trace minerals | mg/kg |
| Cu | 1.7 |
| Fe | 16.8 |
| I | 1.5 |
| Mn | 1.1 |
| Se | 1.6 |
| Zn | 24 |

The water soluble extract is a white powder that is soluble in water at room temperature. It has a biological digestibility index of 95-97% as tested on mink.

This disclosure has been described above generally and also in terms of one or more embodiments so that an understanding of the principles underlying the apparatuses and processes can be obtained. There are, however, many configurations for hydrolysis of a protein containing animal or vegetable raw material not specifically described herein but with which the present disclosure is applicable. The present disclosure should therefore not be seen as limited to the particular embodiments described herein, but rather, it should be understood that it has wide applicability with respect to hydrolysis methods, systems, and apparatus. Moreover, it will be apparent that certain features of each embodiment can be used in combination with methods, systems, or apparatus illustrated or described in other embodiments. Accordingly, the above description should be construed as illustrative, and not in a limiting sense. All modifications, variations, or equivalent arrangements and implementations that are within the scope of the attached claims should therefore be considered within the scope of the invention.

As used herein and in the following claims, singular articles, such as "a," "an," "the", "said" and the like, can mean one or more than one, and are not intended in any way to limit the terms that follow to their singular form, unless expressly noted otherwise. Unless otherwise indicated, any claim which contains the word "or" to indicate alternatives shall be satisfied if one, more than one, or all of the alternatives connected by the word "or" are present in an embodiment which otherwise meets the limitations of such claim.

The present application claims priority from Danish Patent Application Number PA 2002 01859, entitled A PLANT AND A METHOD FOR CONTINUOUS HYDROLYSIS OF A PROTEIN CONTAINING ANIMAL OR VEGETABLE RAW MATERIAL AND APPLICATION OF THE RESULTING HYDROLYSIS PRODUCTS, filed Dec. 2, 2002, the entirety of which is incorporated herein by reference.

We claim:

1. A method for continuous, low emulsion hydrolysis of protein-containing raw material derived from the group consisting of fish, animal, and plant material comprising the steps of:
   a) providing an apparatus comprising a hydrolysis area, an inactivation area, and a separation area;
   b) hydrolyzing said raw material in the hydrolysis area by reacting a reaction mixture comprising said raw material and at least one enzyme present in said hydrolysis area, wherein the reaction mixture contains both solids and liquid, and wherein upon hydrolysis, said reaction mixture further comprises hydrolysis product;
   c) inactivating said reaction mixture from the hydrolysis area in the inactivation area to substantially inactivate the enzyme present in the reaction mixture; and
   d) separating the reaction mixture in the separation area that receives at least a portion of the reaction mixture from the inactivation area and is capable of separating it into two or more components, including at least one substantially liquid component which comprises water-soluble protein; and including at least one substantially solid containing component; wherein the hydrolysis area, inactivation area, and separation area operate in a continuous mode and maintain an even and continuous flow mode of said reaction mixture; and operated such that any emulsion present in said liquid component is present in an amount is maintained below 10% of the reaction mixture.

2. The method of claim 1, wherein the step of separating comprises separating
   the at least a portion of the reaction mixture into at least one substantially liquid component and at least one substantially solid-containing component.

3. The method of claim 1, wherein the level of emulsion present is maintained at or below about 5%.

4. The method of claim 1, wherein the level of emulsion present is maintained at or below about 2%.

5. The method of claim 1, wherein the level of emulsion present is maintained at or below about 1%.

6. The method of claim 1, wherein the level of emulsion present is maintained at or below about 0.5%.

7. The method of claim 1, wherein the step of separating comprises separating the at least a portion of the reaction mixture using a slanted filter screen to yield at least one substantially liquid component and a substantially solid component.

8. The method of claim 7, wherein the slanted filter screen has a mesh size of between about 1 and about 200 mesh.

9. The method of claim 1, wherein the separating step further comprises separating the at least one substantially liquid component into at least a first fraction comprising a water-soluble protein and at least a second fraction comprising a water-insoluble protein.

10. The method of claim 9, wherein the step of separating the at least one substantially liquid component comprises centrifugation.

11. The method of claim 1, wherein the reaction mixture is separated into a first component comprising primarily an aqueous solution, a second component comprising primarily lipids, and a third component comprising primarily solid matter.

12. The method of claim 1, wherein the step of separating comprises pumping the reaction mixture out of the inactivation area.

13. The method of claim 12, wherein at least one of the feeder screws rotates clockwise and counter-clockwise at different times during the separation step.

14. The method of claim 1, wherein the step of hydrolyzing comprises conveying the reaction mixture through the hydrolysis area with at least one feeder screw.

15. The method of claim 1, wherein the step of hydrolyzing comprises hydrolyzing the reaction mixture in a tube-shaped area.

16. The method of claim 1, wherein the step of inactivating comprises conveying the reaction mixture through the inactivation area with at least one feeder screw.

17. The method of claim 1, further comprising the step of pumping oil present in the reaction mixture away from the reaction mixture, or the step of decanting oil present in the reaction mixture, or both.

18. The method of claim 17, wherein oil is pumped away from the hydrolysis area, the inactivation area, or both.

19. The method of claim 1, wherein prior to the step of separating, the reaction mixture in the inactivation area is agitated to substantially suspend solid matter present in the inactivation area.

20. The method of claim 1, wherein prior to the step of hydrolyzing, the protein-containing raw material is collected in pieces in a collection area.

21. The method of claim 20, wherein, prior to hydrolysis, the collected pieces of raw material are processed to reduce the size of the pieces.

22. The method of claim 21, wherein the size of the pieces is from about 15 mm to about 50 mm.

23. The method of claim 21, wherein the size of the pieces is 3.00 mm or more.

24. The method of claim 1, wherein the raw material comprises material derived from fish.

25. The method of claim 1, wherein the raw material is hydrolyzed at a rate of two tons per hour.

26. The method of claim 1, wherein the step of hydrolyzing is carried out as a continuous process.

27. The method of claim 26, wherein the continuous process is capable of continuous hydrolysis for at least seventy-two hours.

28. The method of claim 1, wherein the step of inactivating is carried out as a continuous process.

29. The method of claim 1, wherein the liquid in the reaction mixture is substantially separated from the solids and water soluble protein is obtained from the liquid.

30. The method of claim 29, wherein the yield of water soluble protein obtained from the method is at least about 50 percent by weight of the weight of protein contained in the raw material.

31. The method of claim 29, wherein the yield of water soluble protein obtained from the method is at least about 60 percent by weight of the weight of protein contained in the raw material.

32. The method of claim 29, wherein the yield of water soluble protein obtained from the method is at least about 70 percent by weight of the weight of protein contained in the raw material.

33. The method according to claim 1, wherein said apparatus further includes a pump and wherein the pump, pumps the reaction mixture out the inactivation area and towards the separation areas, such that the liquid emulsion in the reaction mixture is maintained at or below a predetermined level.

34. A method for continuously hydrolyzing a reaction mixture of a protein containing fish, animal or vegetable raw material into a liquid phase (13) and a solid phase (12), comprising the steps of:
  a) providing a plant for the continuous hydrolysis of a reaction mixture of the protein containing animal or vegetable raw material, into at least a liquid phase (13) and at least a solid phase (12) said plant comprising a preparation section (1) a hydrolysis section (4) connected thereto, an inactivation section (7) connected to the hydrolysis section (4) and a final processing section (17) connected to the inactivation section, said hydrolysis section (4) comprising at least one substantially tube-shaped hydrolysis reactor (6) having a first feeder screw (20) for conveying a reaction mixture of enzyme and raw material through the at least one tube-shaped hydrolysis reactor (6) and onward into the inactivation section (7) having at least one inactivation reactor (8) connected to the hydrolysis section (4) with an inlet end (9) and an exit end (10) positioned opposite to it, characterized by the exit end (10) of the at least one inactivation reactor (8) having at last one outlet (14) for the solid phase (12) and at least one outlet (16) for the liquid phase (13) positioned at a distance from the outlet (14) for the solid phase (12) dividing up the raw material; mixing the raw material with the enzyme;
  b) hydrolyzing the raw material enzymatically for a determined period of time in the hydrolysis section;
  c) inactivating the enzymes which are present in the reaction mixture, in the inactivation reactor (8),
  d) letting out continuously the solid phase (12) and the liquid phase (14) from the reaction mixture in the inactivation reactor (8), characterized by the liquid phase (13) comprising a fatty fraction and an aqueous fraction with a content of dissolved and non-dissolved ingredients of protein origin, the fatty fraction and the aqueous fraction being let out from the inactivation reactor (8) continuously either separately at identical or different rates or as a collective homogenized suspension and wherein the hydrolysis section, inactivation section, and separation section operate in a continuous mode and maintain an even and continuous flow mode of said reaction mixture; and
  wherein any emulsion present in said liquid component is maintained below 10% of the reaction mixture.

35. A method according to claim 34, characterized by the dissolved and non-dissolved ingredients of protein origin and the fatty phase subsequently being separated in a tricanter or a decanter.

36. A method according to claim 34, characterized by the method comprising an introductory step in which metal parts are separated out from the raw material.

* * * * *